US010881417B2

(12) United States Patent
Mahfouz

(10) Patent No.: US 10,881,417 B2
(45) Date of Patent: Jan. 5, 2021

(54) PATIENT-SPECIFIC INSTRUMENTATION AND METHODS FOR TOTAL ANKLE REPLACEMENT

(71) Applicant: Zimmer, Inc., Warsaw, IN (US)

(72) Inventor: Mohamed Mahfouz, Knoxville, TN (US)

(73) Assignee: Zimmer, Inc., Warsaw, IN (US)

(*) Notice: Subject to any disclaimer, the term of this patent is extended or adjusted under 35 U.S.C. 154(b) by 514 days.

(21) Appl. No.: 15/177,871

(22) Filed: Jun. 9, 2016

(65) Prior Publication Data

US 2016/0361071 A1 Dec. 15, 2016

Related U.S. Application Data

(60) Provisional application No. 62/173,147, filed on Jun. 9, 2015.

(51) Int. Cl.
*A61B 17/16* (2006.01)
*A61B 17/17* (2006.01)
(Continued)

(52) U.S. Cl.
CPC .......... *A61B 17/1682* (2013.01); *A61B 17/15* (2013.01); *A61B 17/1739* (2013.01); *A61B 17/1775* (2016.11); *A61F 2/4202* (2013.01)

(58) Field of Classification Search
CPC ............ A61F 2/4202; A61F 2002/4205; A61F 2002/4207; A61B 17/1662;
(Continued)

(56) References Cited

U.S. PATENT DOCUMENTS 8,337,503 B2 12/2012 Lian
8,623,026 B2 * 1/2014 Wong ..................... A61B 34/10
606/96
(Continued)

FOREIGN PATENT DOCUMENTS

CN 108472049 A 8/2018
FR 2715557 8/1995
(Continued)

OTHER PUBLICATIONS

"International Application Serial No. PCT/US2016/036652, International Preliminary Report on Patentability dated Dec. 21, 2017", 10 pgs.
(Continued)

*Primary Examiner* — Kevin T Truong
*Assistant Examiner* — Tracy L Kamikawa
(74) *Attorney, Agent, or Firm* — Schwegman Lundberg & Woessner, P.A.

(57) ABSTRACT

A patient-specific pin guide for performing a total ankle arthroplasty can comprise a tibia pin guide, a talus pin guide and an interlocking component. A patient-specific cutting guide system for performing a total ankle arthroplasty can comprise a talus cutting guide and a tibia cutting guide. A method of performing a total ankle arthroplasty can comprise: coupling a patient-specific talus pin guide to a talus; coupling a patient-specific tibia pin guide to a tibia; positioning an interlocking device between the patient-specific tibia pin guide and the patient-specific talus pin guide; inserting guide pins into the patient-specific tibia and talus pin guides; removing the patient-specific talus and tibia pin guides from the guide pins; and coupling patient-specific talus and tibia cutting guides to the talus and tibia using at least some of the guide pins to alternatively perform resections on the tibia and talus.

20 Claims, 27 Drawing Sheets

(51) Int. Cl.
*A61B 17/15* (2006.01)
*A61F 2/42* (2006.01)

(58) Field of Classification Search
CPC ............ A61B 17/1682; A61B 17/1697; A61B 17/1739; A61B 17/1775; A61B 17/15
See application file for complete search history.

(56) References Cited

U.S. PATENT DOCUMENTS

| | | | |
|---|---|---|---|
| 8,808,297 B2* | 8/2014 | Stemniski | A61B 17/15 606/87 |
| 8,884,618 B2 | 11/2014 | Mahfouz | |
| 9,186,154 B2 | 11/2015 | Li | |
| 9,687,250 B2* | 6/2017 | Dayton | A61B 17/15 |
| 2004/0039394 A1 | 2/2004 | Conti et al. | |
| 2008/0287954 A1 | 11/2008 | Kunz et al. | |
| 2013/0116797 A1 | 5/2013 | Coulange et al. | |
| 2014/0188236 A1 | 7/2014 | McGinley et al. | |
| 2014/0265308 A1* | 9/2014 | Reilly | H01R 13/5841 285/153.1 |
| 2014/0324059 A1 | 10/2014 | Stemniski et al. | |
| 2015/0057665 A1* | 2/2015 | Neal | A61B 17/1739 606/87 |
| 2015/0182273 A1* | 7/2015 | Stemniski | A61B 17/88 606/96 |

FOREIGN PATENT DOCUMENTS

| | | |
|---|---|---|
| WO | 2006023824 | 3/2006 |
| WO | 2016201078 | 12/2016 |

OTHER PUBLICATIONS

"International Application Serial No. PCT/US2016/036652, Invitation to Pay Add'l Fees and Partial Search Report dated Nov. 18, 2016", 20 pgs.

"International Application Serial No. PCT/US2016/036652, International Search Report dated Feb. 6, 2017", 9 pgs.

"International Application Serial No. PCT/US2016/036652, Written Opinion dated Feb. 6, 2017", 8 pgs.

"European Application No. 16730209.0, Response filed Aug. 23, 2018 to Office Action dated Feb. 13, 2018", 16 pgs.

* cited by examiner

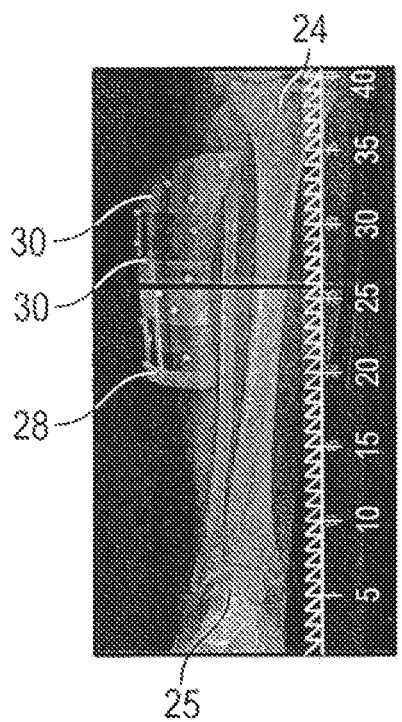 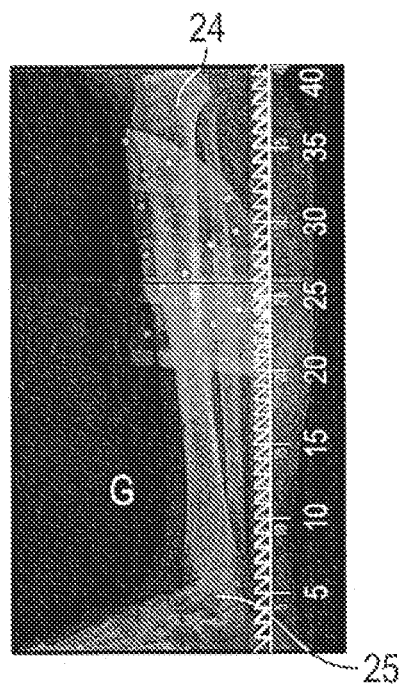
FIG. 3A    FIG. 3B
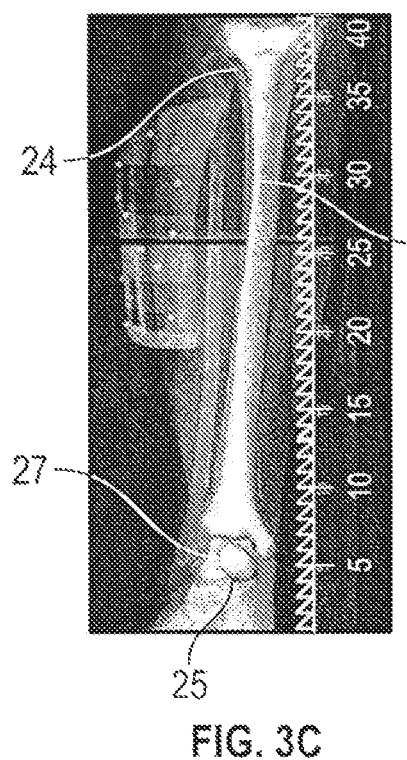 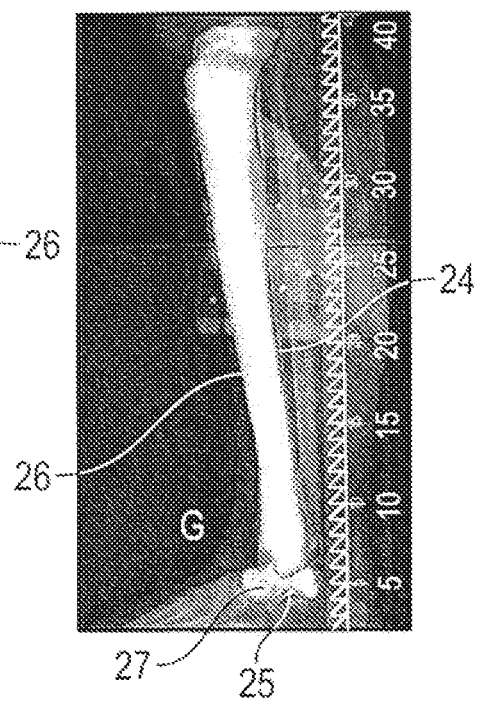
FIG. 3C    FIG. 3D

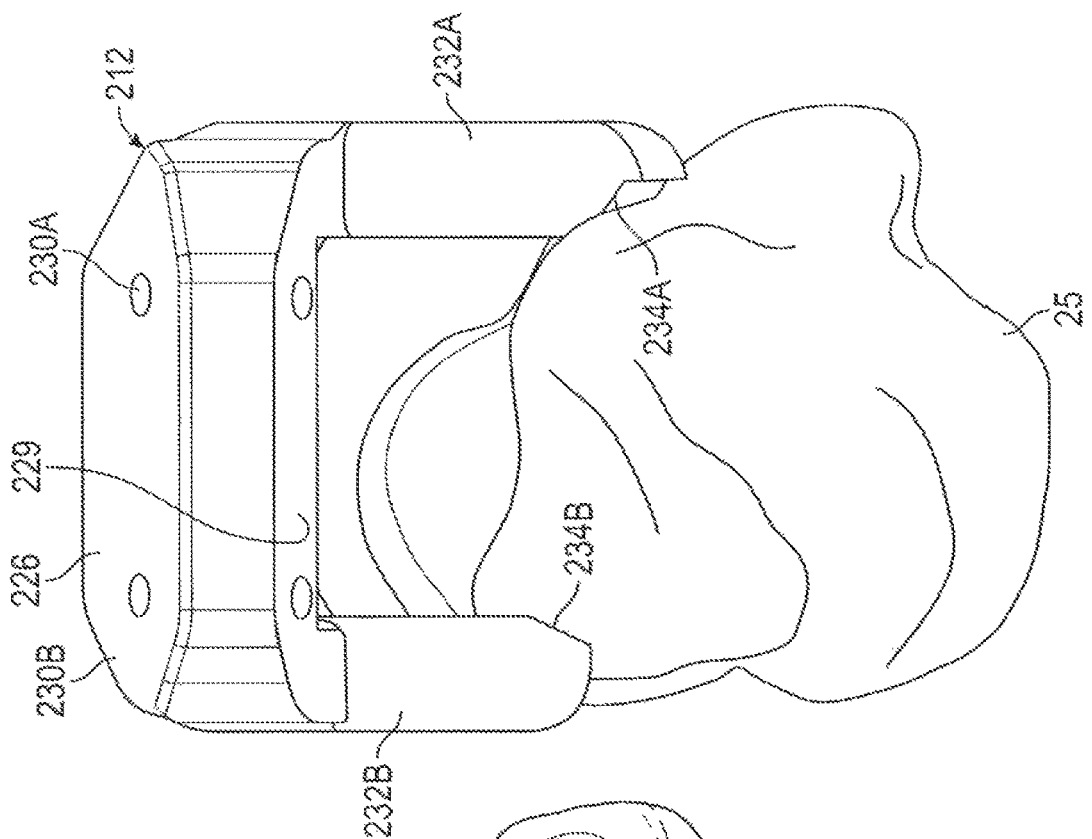
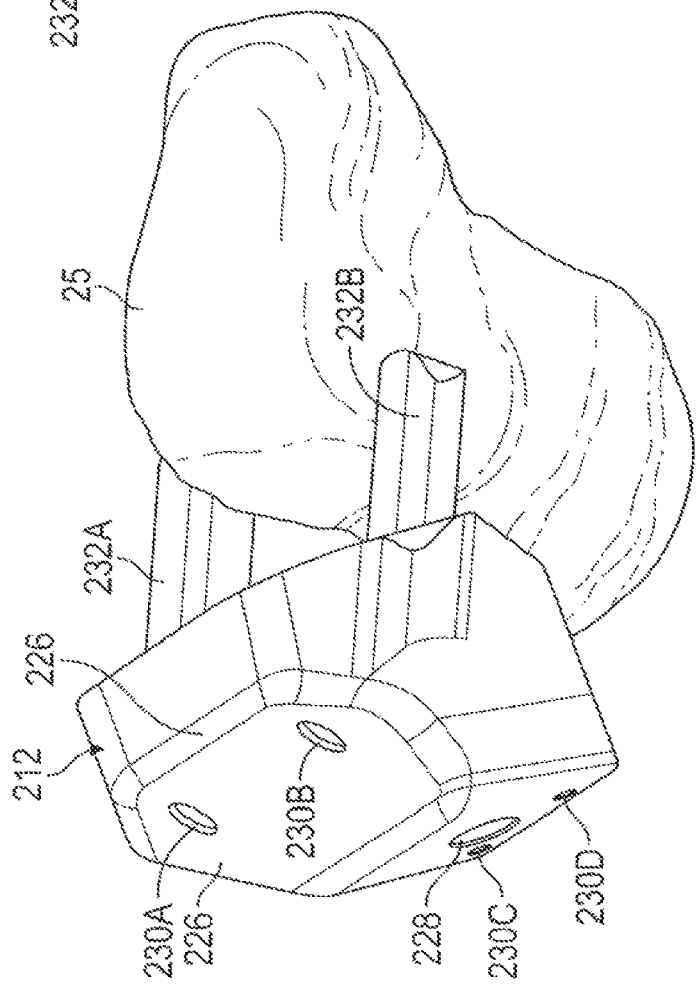
FIG. 18A
FIG. 18B

PATIENT-SPECIFIC INSTRUMENTATION AND METHODS FOR TOTAL ANKLE REPLACEMENT

CLAIM OF PRIORITY

This patent application claims the benefit of priority of U.S. Provisional Patent Application Ser. No. 62/173,147 to Mahfouz, entitled "PATIENT SPECIFIC INSTRUMENTATION FOR TOTAL ANKLE REPLACEMENT," filed on Jun. 9, 2015, which is hereby incorporated by reference herein in its entirety.

BACKGROUND

The present disclosure is directed to apparatus and methods for use with ankle arthroplasty including total ankle replacement.

Patient specific instruments have been successfully deployed for multiple surgical procedures. By creating 3D models of the patient anatomy from medical images, the surgery can be customized using virtual 3D surgical planning resulting in the creation of patient-specific cutting guides, which fit over the patient anatomy allowing for precise replication of the planned surgery as compared to arthroplasty with conventional instrumentation.

U.S. Pat. No. 8,337,503 to Lian describes cutting guides and instruments for use in total ankle replacement surgery.

OVERVIEW

The present inventors have recognized, among other things, that a problem to be solved can include designing ankle cutting guides that achieve adequate contact with the various bones in an ankle joint, i.e., the tibia and the talus. For example, a one-piece cutting guide for a tibia and talus can lack the proper support for supporting the talus, and performing the tibia resection can remove portions of the bone desired for adequate bone interface. The present subject matter can help provide a solution to this problem, such as by providing either multiple independent cutting guides that can assist in cutting each of the bones independently, or by providing multi-component pin guides and cutting guides that can be selectively disassembled and assembled to provide different co-operating guide instruments for performing tibia and talus resections. The present subject matter can also utilize patient-specific instruments to improve bone contact for both anterior and lateral total ankle replacement approaches.

In an example, a patient-specific pin guide for performing a total ankle arthroplasty can comprise a tibia pin guide, a talus pin guide and an interlocking component. The tibia pin guide can comprise a first patient-specific surface for engaging a surface of a tibia, at least one tibia pin hole extending through the tibia pin guide, and a socket extending through the tibia pin guide. The talus pin guide can comprise a second patient-specific surface for engaging a surface of a talus, and at least one talus pin hole extending through the talus pin guide. The interlocking component can extend through the socket to position the tibia pin guide relative to the talus pin guide.

In another example, a patient-specific cutting guide system for performing a total ankle arthroplasty can comprise a talus cutting guide and a tibia cutting guide. The talus cutting guide can comprise a talus main body, a talus extension extending from the talus main body and having a first patient-specific surface configured to engage a surface of a tibia, and a cutting body extending from the talus main body in an opposite direction as the talus extension, the cutting body having a first cutting guide slot positioned to resect a talus. The tibia cutting guide can comprise a tibia main body having a second cutting guide slot positioned to resect a tibia, a tibia extension having a second patient-specific surface configured to engage the surface of a tibia, and a flange forming a third cutting guide slot with the tibia main body.

In an additional example, a method of performing a total ankle arthroplasty can comprise: coupling a patient-specific talus pin guide to a talus; coupling a patient-specific tibia pin guide to a tibia; positioning an interlocking device between the patient-specific tibia pin guide and the patient-specific talus pin guide; inserting guide pins into the patient-specific tibia and talus pin guides; removing the patient-specific talus and tibia pin guides from the guide pins; and coupling patient-specific talus and tibia cutting guides to the talus and tibia using at least some of the guide pins to alternatively perform resections on the tibia and talus.

This overview is intended to provide an overview of subject matter of the present patent application. It is not intended to provide an exclusive or exhaustive explanation of the invention. The detailed description is included to provide further information about the present patent application.

BRIEF DESCRIPTION OF THE DRAWINGS

FIGS. 3A and 3B are A-P and lateral views of X-ray images of a tibia and talus.

FIGS. 3C and 3D are A-P and lateral views of the X-ray images of FIGS. 3A and 3B, respectively, showing virtual models of the tibia and talus overlaid on top of the tibia and talus in the X-ray images.

FIGS. 18A and 18B are perspective and superior views of a talus showing placement and anatomical contacts of a talus pin guide of FIGS. 17A and 17B.

Figure 1:
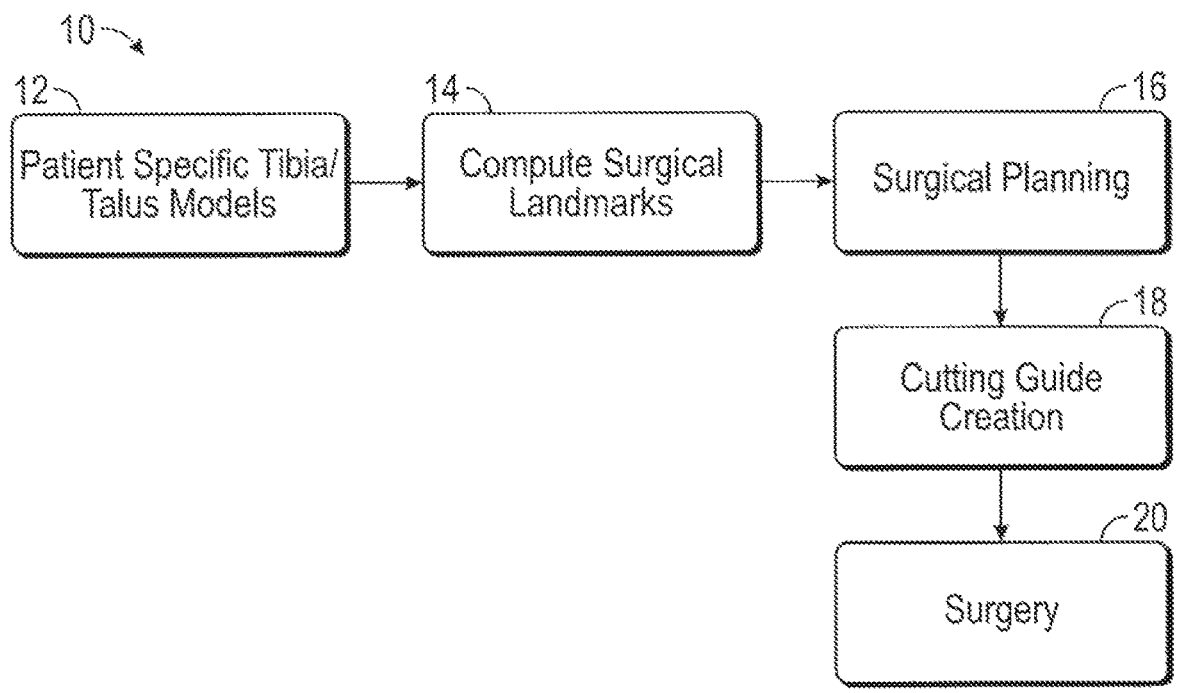
FIG. 1 is a flow diagram of a process for producing a patient-specific instrument (PSI) according to an embodiment the present disclosure.

In the drawings, which are not necessarily drawn to scale, like numerals may describe similar components in different views. Like numerals having different letter suffixes may represent different instances of similar components. The drawings illustrate generally, by way of example, but not by way of limitation, various embodiments discussed in the present document.

DETAILED DESCRIPTION

It should be understood that the following detailed description of embodiments of the present invention are exemplary in nature and are not intended to constitute limitations upon the present invention. It is also to be understood that variations of the exemplary embodiments contemplated by one of ordinary skill in the art shall concurrently fall within the scope and spirit of the invention.

FIG. 1 is a flow diagram of process 10 for producing a patient-specific instrument (PSI) according to an example the present disclosure. Process 10 can include generation of patient-specific (or mass customized) Tibia/Talus models at step 12, surgical landmarking at step 14, surgical planning at step 16, cutting guide creation at step 18 and surgery at step 20. Additional details and description of procedures, systems and methods that can be used in process 10, particularly with respect to the generation of patient-specific surfaces, are described in U.S. Pat. No. 8,884,618 to Mahfouz, which is hereby incorporated by reference herein in its entirety.

At step 12, creation of a patient-specific (or mass customized) cutting guide from images can begin with the creation of a three dimensional model or other representation of the patient anatomy using two dimensional images (or data). The models can be reconstructed using different modalities (X-ray or CT). The basis for the creation of the patient-specific (or mass customized) bone models of step 12 can be capturing the morphological variation in both tibia and talus, which can be done using a statistical atlas as described in greater details below.

Figure 2:
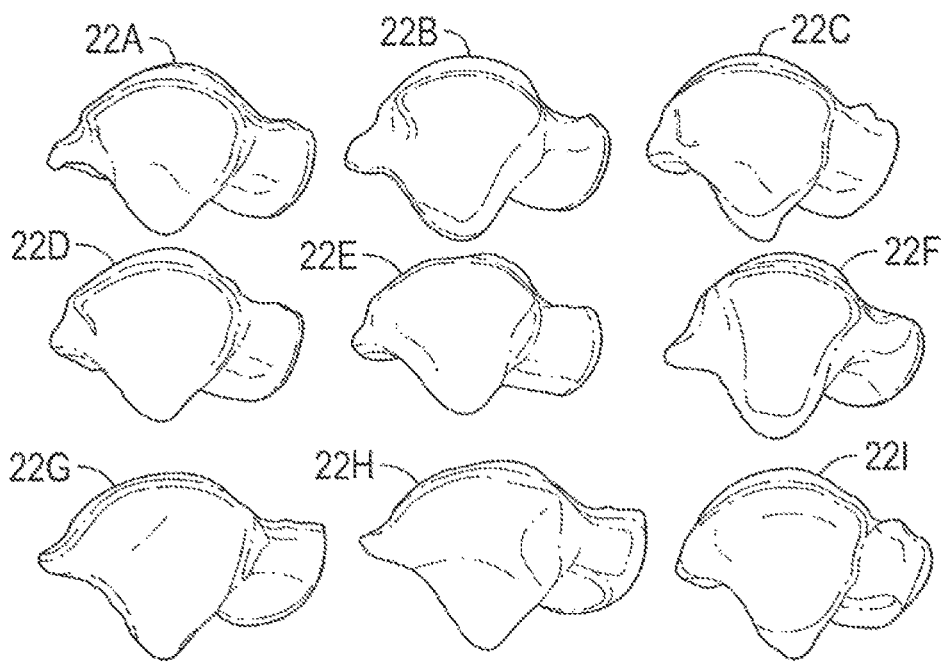
FIG. 2 is a diagram showing a plurality of talus bones comprising a portion of an exemplary statistical atlas in accordance with the present disclosure.

FIG. 2 is a diagram showing a plurality of talus bones 22A-22I comprising a portion of a statistical atlas in accordance with the present disclosure. FIG. 2 illustrates the varying geometry of the anatomy of various talus bones that can be aggregated into a statistical database or atlas. In other embodiments, a statistical atlas can be made from a plurality of talus or tibia bone models that are modeled from actual talus and tibia bones from patients having characteristics from a variety of demographics and characteristics.

Statistical atlases can be developed for both the distal tibia and the talus. A statistical atlas can capture the normal morphological variation among healthy bones in both Caucasian and African American populations, which may include more or less than a dataset of 700 bones. These atlases can be used in the reconstruction of patient-specific (or mass customized) anatomy from X-rays and/or 3D segmentation from CT images in step 12. A pathological examination can be carried out on the bone images to capture areas of osteophyte growth in both the talus and the distal tibia. The osteophyte areas can be added to applicable bone models, which can then be used to determine the placement of the patient-specific (or mass customized) instruments using one or both of the bone models and two dimensional images (e.g., X-rays, CTs, MRIs, ultrasound, etc.).

FIG. 3A shows an X-ray image of tibia 24 and talus 25 from an A-P perspective. FIG. 3B shows an X-ray image of tibia 24 and talus 25 from a lateral perspective. FIG. 3C shows tibia 24 overlayed with tibia model 26 and talus 25 overlayed with talus model 27 in the A-P perspective. FIG. 3D shows tibia 24 overlayed with tibia model 26 and talus 25 overlayed with talus model 27 in the lateral perspective. The X-ray images of FIGS. 3A-3D can include the use of reference sleeve 28, which can include markers 30 used to determine the scale of the images relative to the size of the bones, as is known in the art.

In accordance with the instant disclosure, a three phase development of the bone models 26 and 27 can include creation of a segmentation module for extracting patient-specific (or mass customized) models from CT. The segmentation module can allow for validation of bone landmarking, surgical planning and jig (e.g. cutting guides) generation modules, along with building a pathological database for the ankle joint. The second phase can include development of an X-ray reconstruction module for both distal tibia and talus. The third phase can include development of an X-ray and ultrasound registration module. Patient specific (or mass customized) talus and tibia virtual three dimensional models can be created from multiple modalities including CT, MRI, X-ray, ultrasound or a combination of those modalities.

Figure 4A:
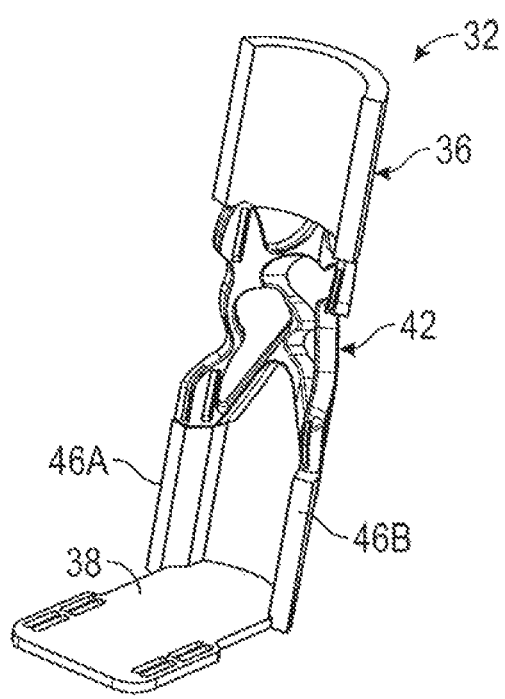
FIGS. 4A and 4B are front and rear perspective views of an X-ray imaging brace with an integrated x-ray calibration target that sets the foot in a neutral position.
Figure 4B:
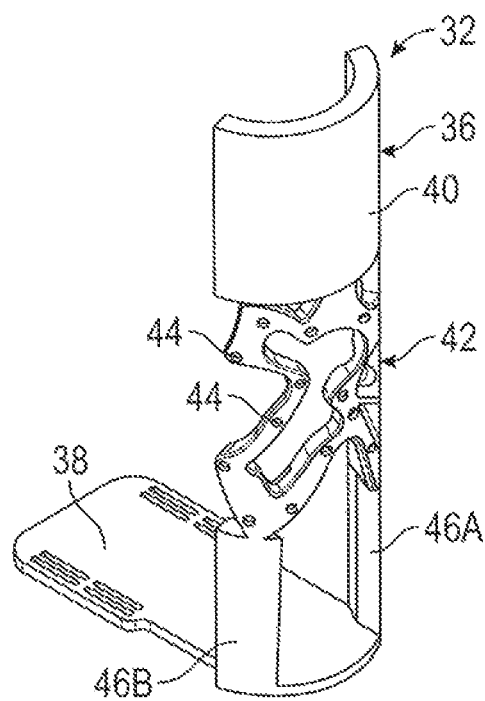
Figure 4C:
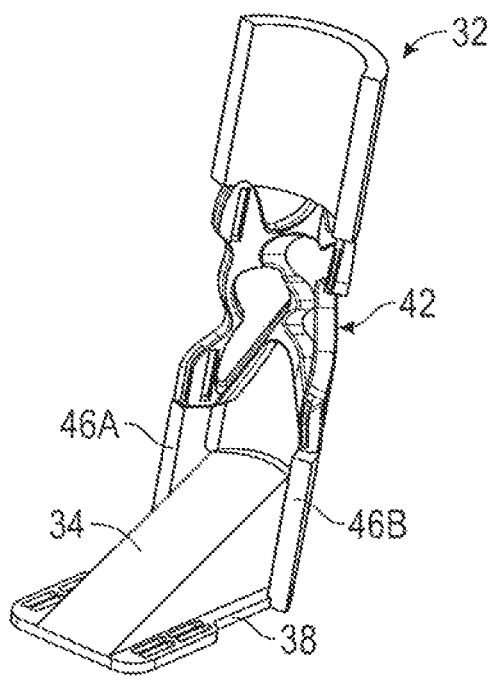
FIGS. 4C and 4D are front and rear perspective views of an X-ray imaging brace with an integrated x-ray calibration target that sets the foot in twenty degrees of plantar flexion.
Figure 4D:
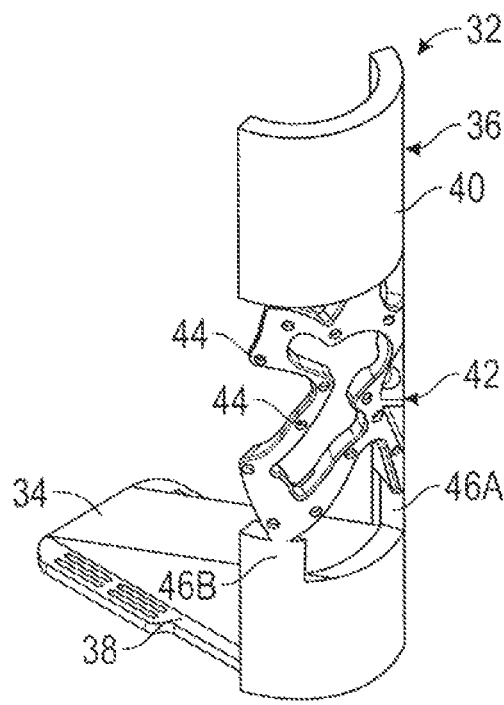

FIGS. 4A and 4B are front and rear perspective views of X-ray imaging brace 32 forming an integrated X-ray calibration target that sets the foot in a neutral position. FIGS. 4C and 4D are front and rear perspective views of X-ray imaging brace 32 having wedge 34 forming an integrated X-ray calibration target that sets the foot in twenty degrees of plantar flexion. Brace 32 can include calf sleeve 36 and foot rest 38. Calf sleeve 36 can include upper sleeve 40, middle web 42 having markers 44 and lower struts 46A and 46B.

As part of performing X-ray reconstruction, a patient's lower leg (near the calf) can be outfitted with brace 32 featuring radio opaque beads or markers 44, as shown in FIGS. 4A-4D. With the patient standing anteroposterior and lateral, X-ray images are taken of the tibia and foot. These X-ray images can be segmented to define contours of the talus and tibia. The segmented images can then be utilized to construct virtual, three-dimensional patient-specific (or mass customized) models of the tibia and talus, such as those shown in FIG. 3C-3D.

To increase the accuracy of the X-ray reconstruction (taking 2D images and creating a virtual 3D model), a hybrid approach may be utilized that makes use of ultrasound imaging to capture the surface of the non-occluded bone. Ultrasound can be utilized to capture the areas where the patient-specific (or mass customized) instrument will mate with the patient bone. This approach can enhance the accuracy of the interface between the patient anatomy and the generated patient-specific (or mass customized) instruments.

With reference to step 14, surgical landmarking is the process of taking a model of patient anatomy and outputting patient-specific (or mass customized) surgically relevant landmarks automatically. These landmarks can be verified in the surgical planner.

Figure 5A:
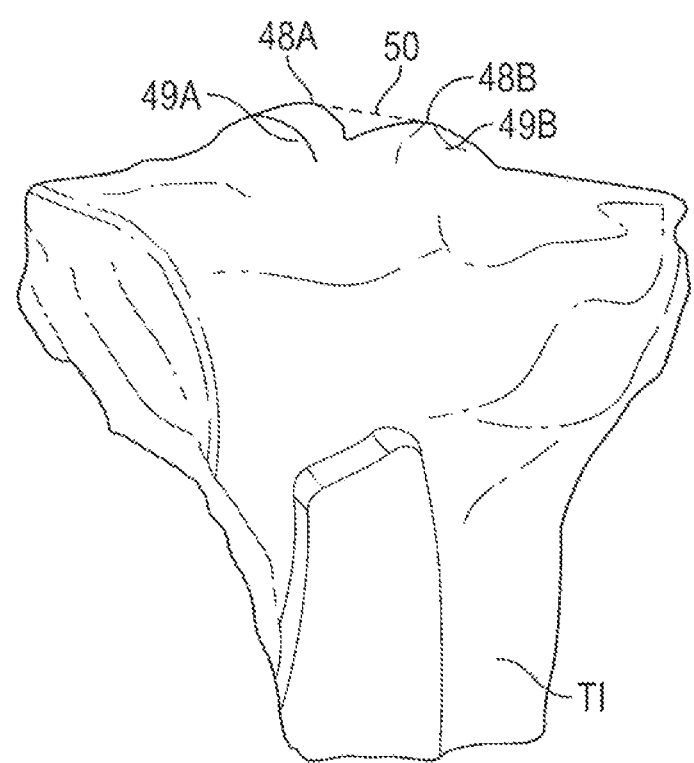
FIG. 5A-5E are various views of a tibia and a fibula showing various anatomic landmarks that can be used in generating virtual models for producing the patient-specific instruments of the present application.

FIG. 5A is an anterior view of a proximal end of tibia TI showing landmarks including intercondylar eminence points 48A and 48B and eminence midpoint 50. Intercondylar eminence points 48A and 48B comprise the two highest projecting points on the medial and lateral intercondylar eminences 49A and 49B, respectively. Eminence midpoint 50 comprises the midpoint of the line between the lateral and medial intercondylar eminence points 48A and 48B.

Figure 5B:
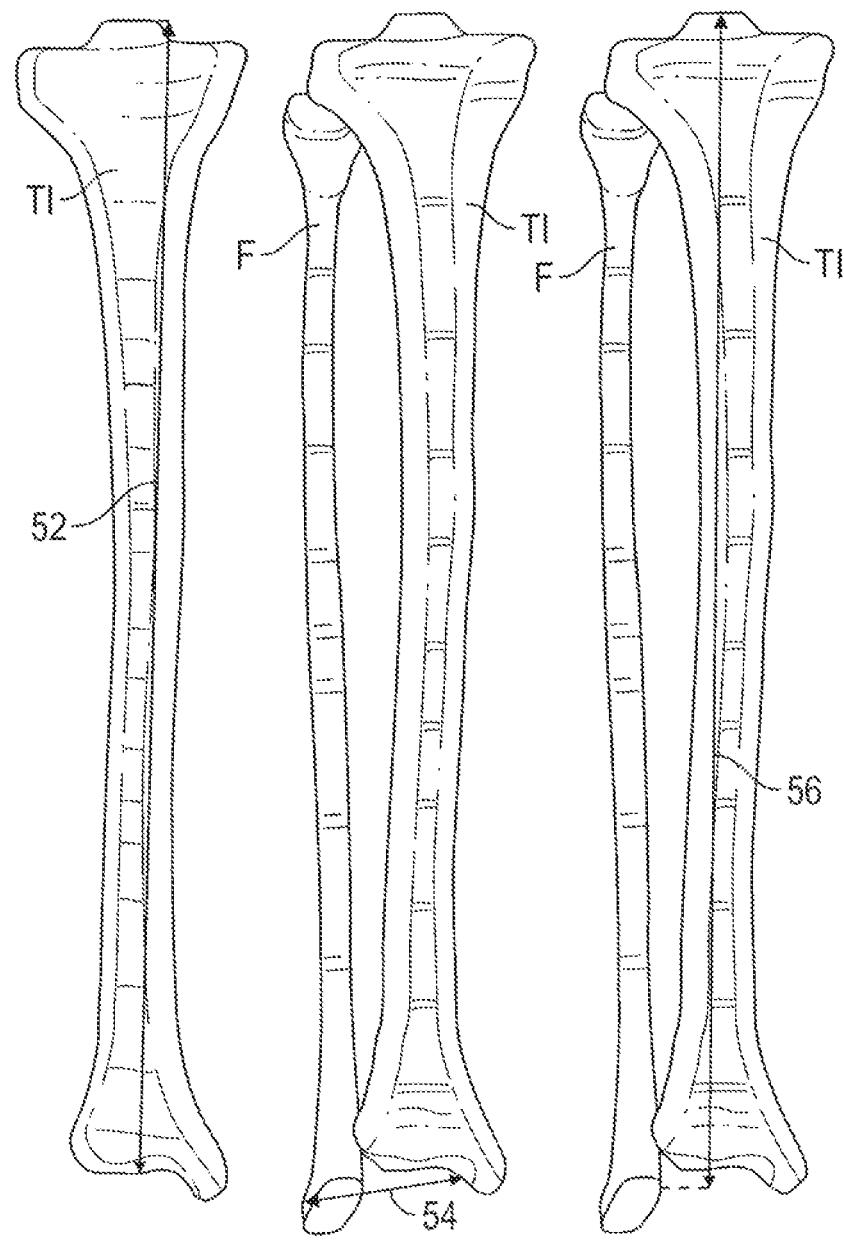

FIG. 5B is an anterior view of tibia TI and fibula F showing landmarks including Anatomical Axis of the Tibia (AAT) 52, Ankle Joint Center 54 and Ankle Joint Mechanical Axis 56.

Anatomical Axis of the Tibia (AAT) 52 comprises the axis is defined by taking the cross-sections of the middle half of tibia shaft every 5%, determining the center of each cross-section, and then fitting a best fit line (Degree 1) to the center of all tibial shaft cross-sections. Ankle Joint Center 54 comprises the midpoint of the line connecting the most medial point of the medial malleolus and most lateral aspects of the lateral malleolus. Ankle Joint Mechanical Axis 56 comprises the axis between the Ankle Joint Center and the Intercondylar Eminence Midpoint.

Figure 5C:
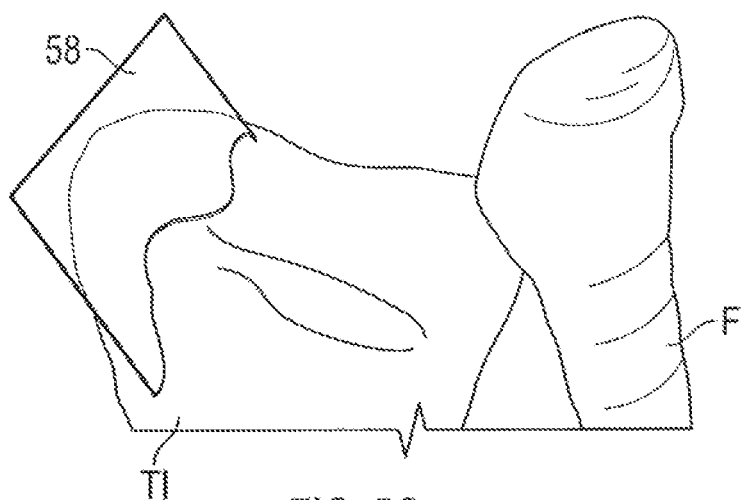
Figure 5D:
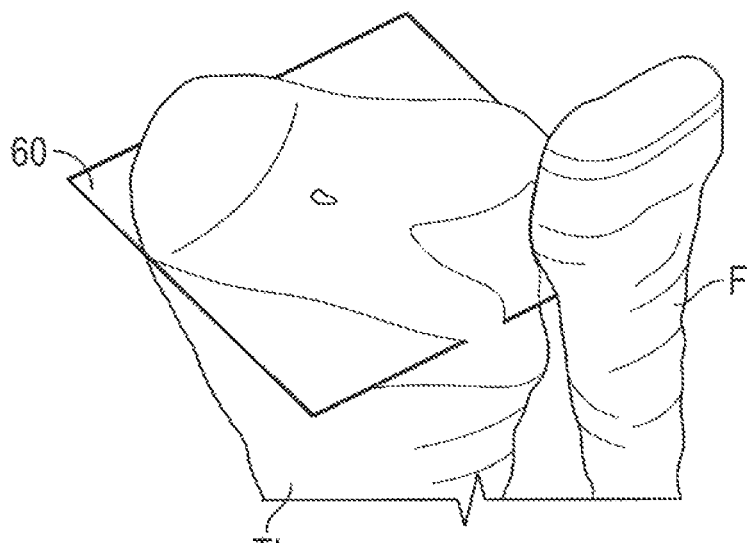
Figure 5E:
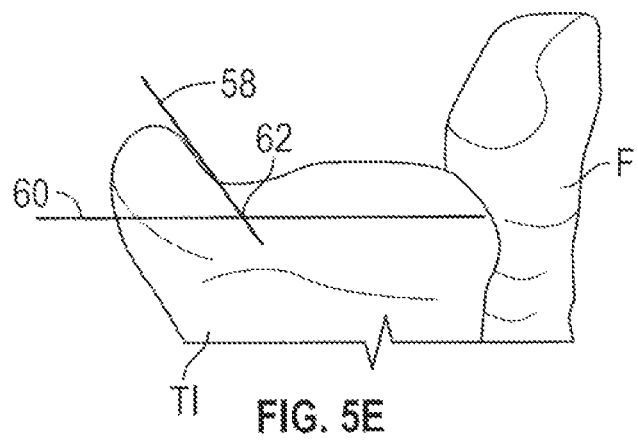

FIG. 5C-5D are anterior views of tibia TI showing landmarks including Medial Malleolus Lateral Plane 58, Distal Tibial Articulating Plane 60 and Tibial Gutter 62.

Medial Malleolus Lateral Plane 58 comprises the lateral surface of the medial malleolus, as defined by plane composed of the best fit plane for the lateral edge of the medial malleolus talus articulating surface. Distal Tibial Articulating Plane 60 comprises the plane normal to the mechanical axis and passing through the deepest point of the distal tibial articulating surface. Tibial Gutter 62 comprises the intersection of Medial Malleolus Lateral Plane 58 and Distal Tibial Articulating Plane 60.

Figure 6B:
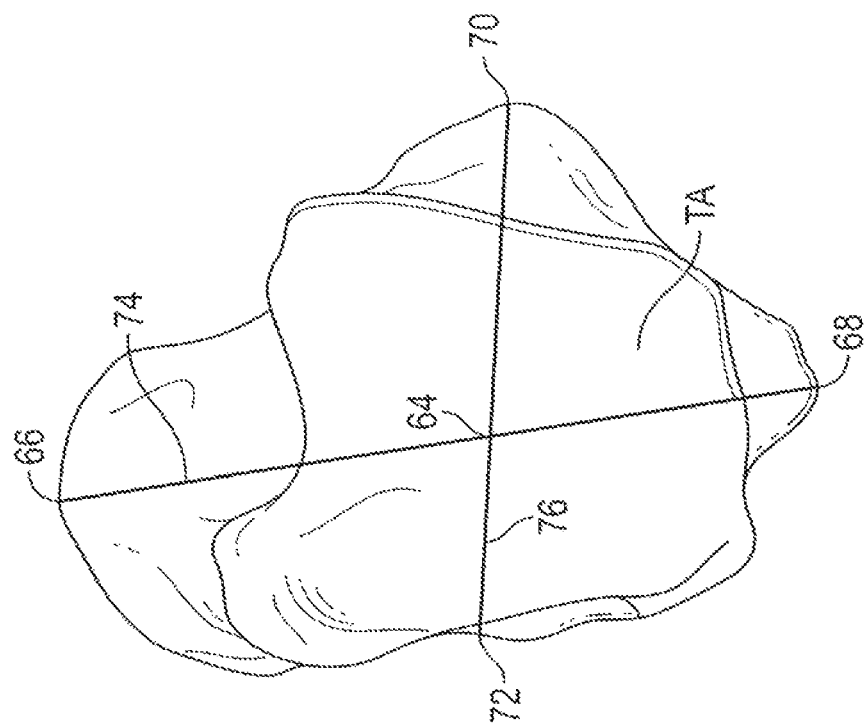
FIGS. 6A and 6B are superior views of a talus showing various anatomic landmarks that can be used in generating virtual models for producing the patient-specific instruments of the present application.
Figure 6A:
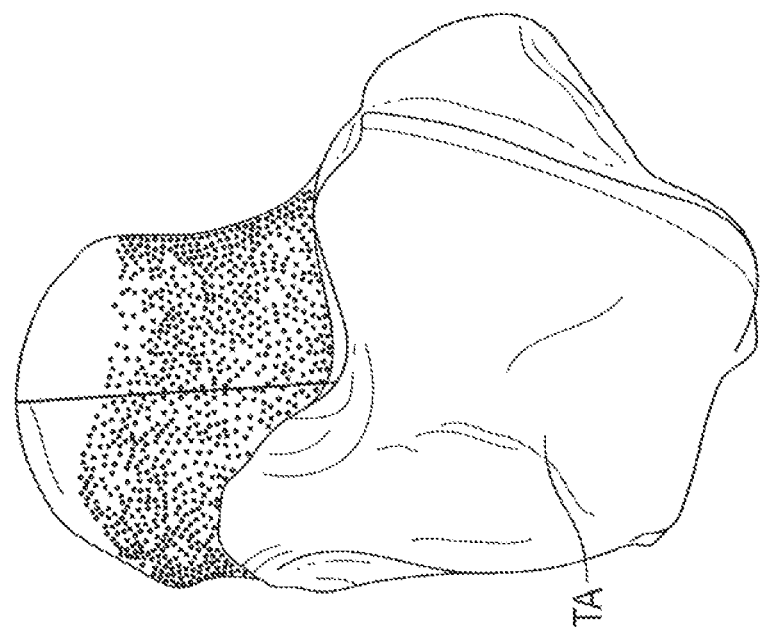

Other landmarks that can be used include the Medial Malleolus Most Media Point and the Lateral Malleolus Most Lateral Point. The Medial Malleolus Most Media Point comprises the most medial point of the medial malleolus. The Lateral Malleolus Most Lateral Point comprises the most lateral point on the lateral malleolus FIGS. 6A and 6B are superior views of talus TA showing landmarks including Talus Center 64, Talus Most Anterior point 66, Talus Most Posterior Point 68, Talus Most Lateral Point 70, Talus Most Medial Point 72.

Talus Center 64 comprises the mean point of the talus bone. Talus Most Anterior Point (TMAP) 66 comprises the most anterior point on the head of the talus TA. Talus Most Posterior Point (TMPP) 68 comprises the most posterior point on the trigonal process. Talus Most Lateral Point (TMLP) 70 comprises the most lateral point on the articular facet for the lateral malleolus of the fibula. Talus Most Medial Point (TMMP) 72 comprises the most medial point on the medial side of the talus trochlea.

Other landmarks include Talus AP Axis (T_AP) 74 (the axis joining TMAP and TMPP), Talus Initial ML Axis (T_I_ML) 76 (the axis joining TMLP and TMMP), Talus SI Axis (the cross product of T_AP and T_I_ML), Talus ML Axis (the cross product of T_AP and T_SI) and Talus most proximal point (the most proximal point on talus trochlea in talus SI direction).

The various landmarks shown in FIGS. 5A-6B illustrate the general location of such landmarks with reference to a typical tibia bone TI or a typical talus bone TA. In practice, the landmarks can be measured from the specific bones of the patient, such as tibia 24 and talus 25 (FIGS. 3A and 3B), or the specific bone models of the patient, such as tibia model 26 and talus model 27 (FIGS. 3C and 3D). The various landmarks illustrated in FIGS. 5A-6B can be used by the surgical planner in generating the models, such as tibia model 26 and talus model 27 (FIGS. 3C and 3D) which can be used to produce patient-specific surfaces of the patient-specific instruments described herein.

With reference to step 16, the surgical planner is an interface whereby the surgeon can view, modify and approve a patient-specific (or mass customized) surgery by manipulating component positioning, obtaining quantitative feedback on position and approve final component position. Component position and orientation can be used to create the patient-specific (or mass customized) instruments.

Figure 13:
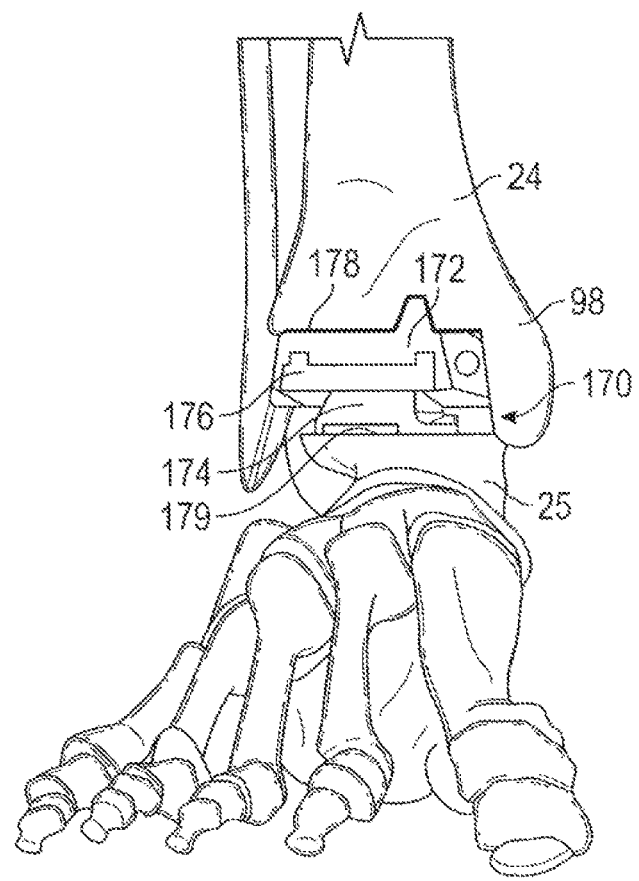
FIG. 13 is a front view of a tibia and talus having implanted therein a conventional total ankle replacement prosthetic via an anterior approach to total ankle replacement.

Surgical planning capitalizes on the power of statistical atlases to provide the user with automatic planning that can be verified and confirmed by the user as input to the surgical planning. A surgical planner interface allows the user to choose implant family and size. The software system can provide the user with default placement based on anatomical landmarks. The user can manipulate the placement to achieve the desired surgical plan. Surgical planning can be conducted by first validating tibia and talus landmarks, followed by virtual placement of the implants on the resected bone surface, for example as can be modeled as shown in FIG. 13.

At step 18, the patient-specific (or mass customized) instrument guide creation software provides automated placement of guide components on the patient anatomy subtracts anatomical geometry from components and outputs patient-specific (or mass customized) instrument models for manufacturing. These models can be approved by an engineer and sent to an approved additive manufacturing facility.

A patient-specific (or mass customized) cutting guide is created for the tibia and talus, where each cutting guide utilizes patient-specific (or mass customized) bone anatomy (avoiding cartilage areas) to provide a solid, unambiguous interface between the guide and cutting tool to lock for the cutting tool in its intended path and orientation.

Figure 7:
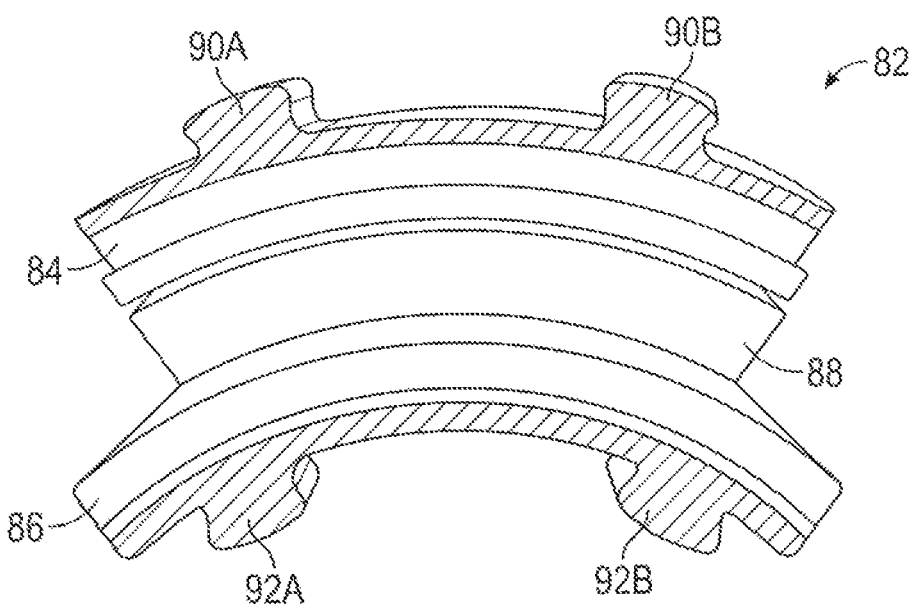
FIG. 7 is a side view of an example of a conventional total ankle replacement prosthetic for a lateral approach to total ankle replacement.

FIG. 7 is a side view of an example of a conventional total ankle replacement prosthetic 82 for a lateral approach to total ankle replacement. Prosthetic 82 can include tibia component 84, talus component 86 and bearing component 88. Tibia component 84 can include posts 90A and 90B for implanting into tibia 24. Talus component 86 can include posts 92A and 92B for implanting into talus 25.

Figure 8:
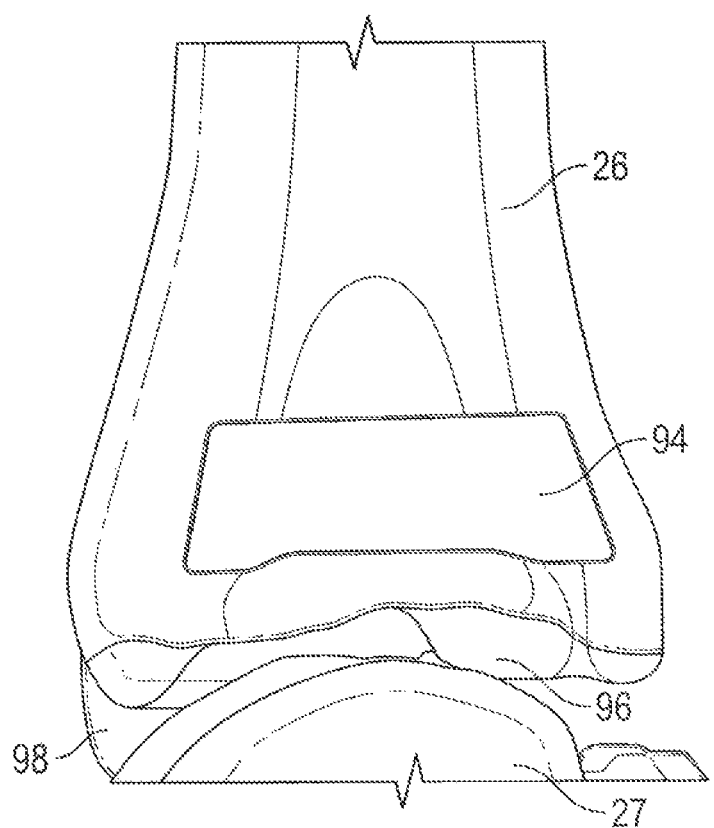
FIG. 8 is a lateral view of a distal tibia model including a highlighted area where a patient-specific or mass customized cutting guide can be matched.

FIG. 8 is a lateral view of distal tibia model 26 including highlighted area 94 where a patient-specific or mass customized cutting guide can be matched. A lateral approach to total ankle arthroplasty involves milling the distal tibia and talus in predefined arcs, as can be defined by the curvature of prosthetic 82 at tibia component 84 and talus component 86, respectively (see FIG. 7). Tibia model 26 can include distal most surface 96 and medial malleolus 98. The surface of tibia 24 represented by distal most surface 96 can be shaped, such as by using cutting guide 100 of FIGS. 9A and 9B, with an arcuate surface extending from the lateral surface at highlighted area 94 to short of medial malleolus 98. As such, tibia model 26 can include surface feature contours similar to those of tibia 24 that are generated during the modeling process to allow the patient-specific instruments described herein to achieve a closely conforming, patient-specific fit.

Figure 9A:
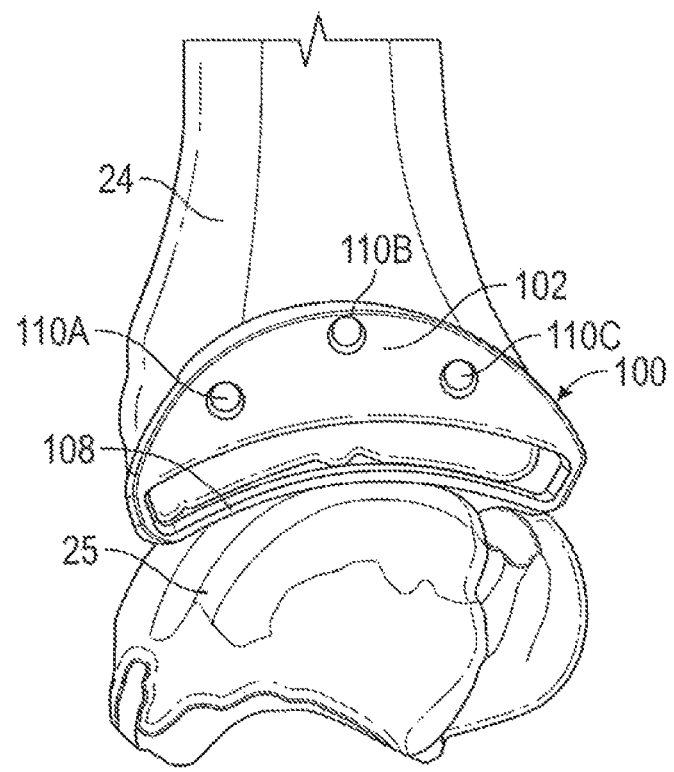
FIGS. 9A and 9B are lateral and elevated proximal perspective views of a distal tibia and a talus showing the position of a patient-specific or mass customized tibia cutting guide with respect to the tibia.
Figure 9B:
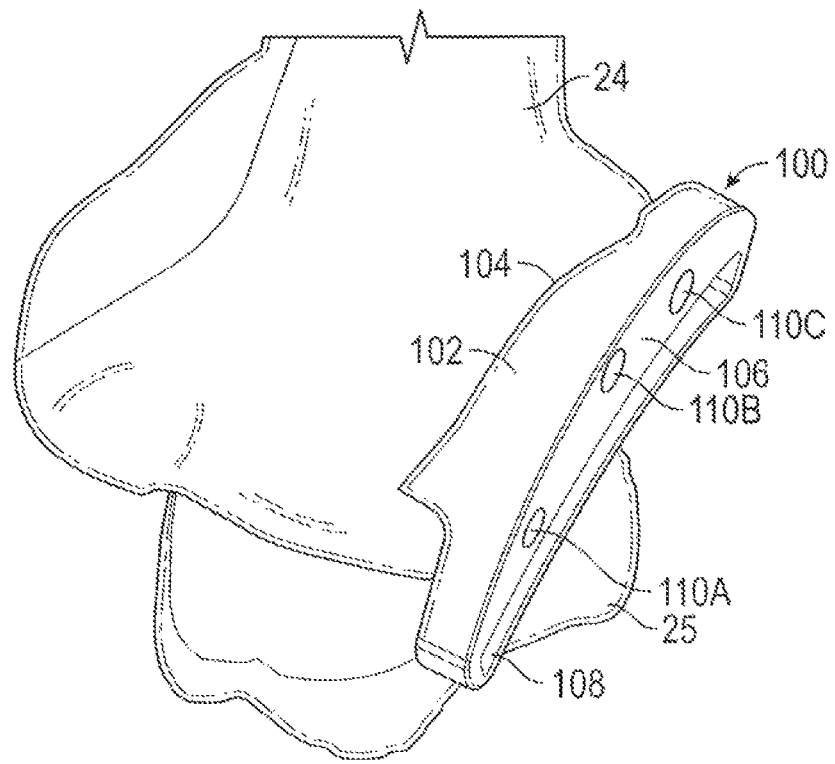

FIGS. 9A and 9B are lateral and elevated proximal perspective views of distal tibia 24 and talus 25 showing the position of patient-specific, or mass customized, tibia cutting guide 100. Tibia cutting guide 100 can include main body 102 having patient-specific surface 104, guide surface 106, cutting slot 108 and pin holes 110A, 110B and 110C. Patient-specific surface 104 can comprise an irregularly shaped surface having contours that closely match with or form a mirror image of highlighted area 94 of tibia model 26, which will closely conform to the corresponding portion of tibia 24 (FIGS. 3A and 3B). Cutting slot 108 can extend along an arcuate path corresponding to the shape of tibia component 84 of prosthetic 82. Pin holes 110A-110C can be used to attach main body 102 to tibia 24 in conjunction with a cutting instrument. For example, a plurality of pins can be inserted into tibia 24 through pin holes 110A-110C and a cutting instrument can be guided over the pins to engage slot 108.

Figure 10:
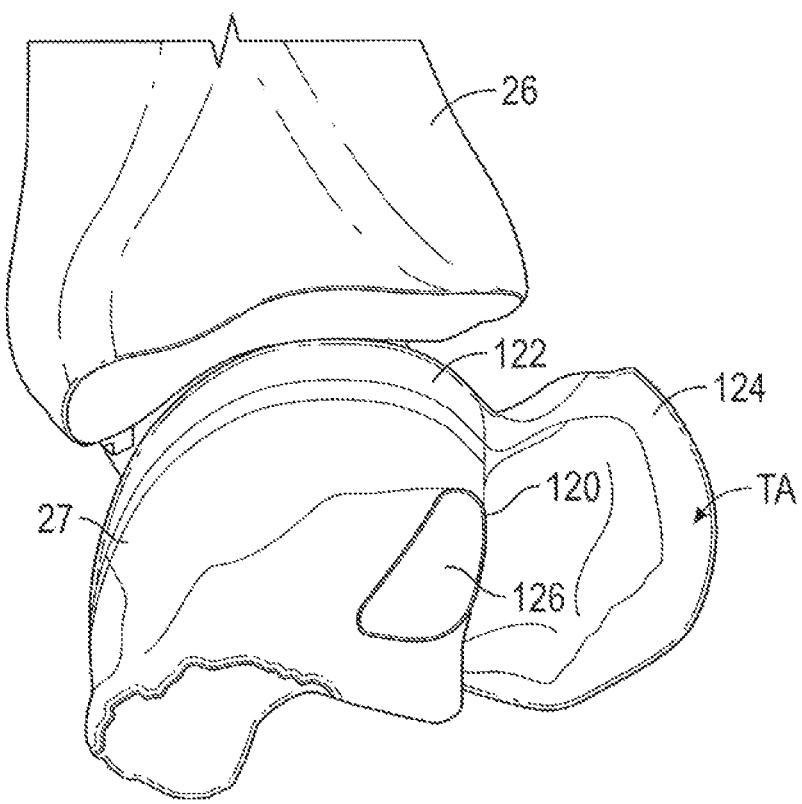
FIG. 10 is a lateral perspective view of a tibia model and a talus model including a highlighted area where a patient-specific or mass customized cutting guide can be matched.

FIG. 10 is a lateral perspective view of tibia model 26 and talus model 27 including highlighted area 120 where a patient-specific or mass customized cutting guide can be matched. Talus model 27 can include articular dome 122, head 124 and lateral process 126. Articular dome 122 can be shaped, such as by using cutting guide 128 of FIGS. 11A and 11B, with an arcuate surface extending from the lateral surface at highlighted area 120 to short of medial malleolus 98 (FIG. 8) of tibia model 26.

Figure 11A:
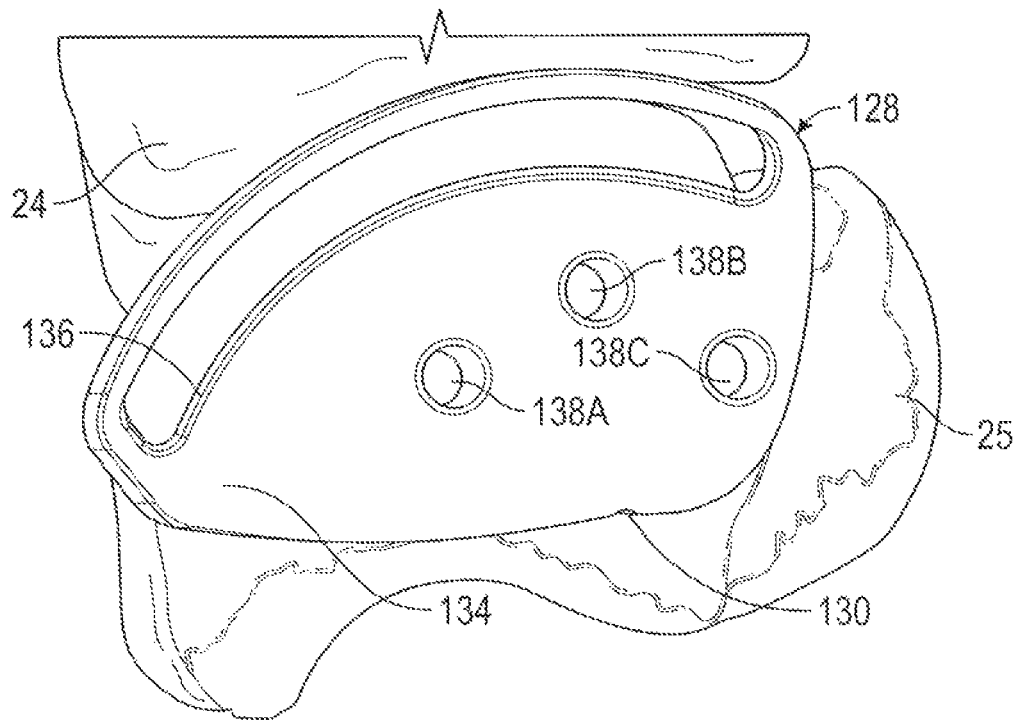
FIGS. 11A and 11B are lateral and rear perspective views of a distal tibia and a talus showing the position of a patient-specific or mass customized talus cutting guide with respect to the talus.
Figure 11B:
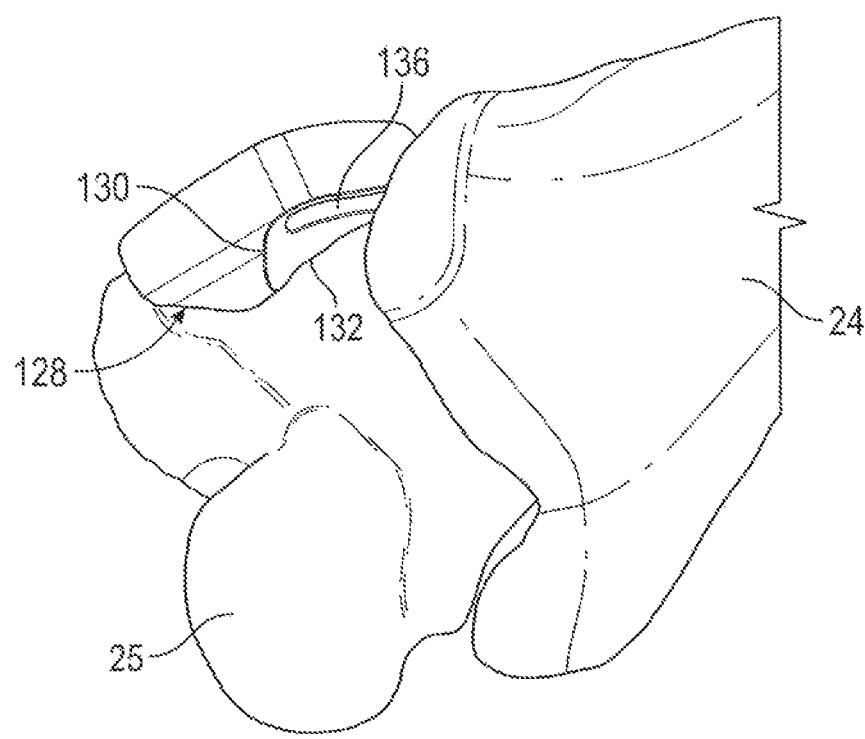

FIGS. 11A and 11B are lateral and rear perspective views of distal tibia 24 and talus 25 showing the position of a patient-specific, or mass customized, talus cutting guide 128. Talus cutting guide 128 can include main body 130 having patient-specific surface 132, guide surface 134, cutting slot 136 and pin holes 138A, 138 and 138C. Patient-specific surface 132 can comprise an irregularly shaped surface having contours that closely match with or form a mirror image of highlighted area 120 of talus model 27, which will closely conform to the corresponding portion of talus 25 (FIGS. 3A and 3B). Cutting slot 136 can extend along an arcuate path corresponding to the shape of talus component 86 of prosthetic 82. Pin holes 138A-138C can be used to attach main body 130 to talus 25 in conjunction with a cutting instrument. For example, a plurality of pins can be inserted into talus 25 through pin holes 138A-138C and a cutting instrument can be guided over the pins to engage slot 136.

FIGS. 8 and 10 show areas of patient anatomy, as represented via tibia and talus models 26 and 27 that are utilized to create patient-specific (or mass customized) cutting guides 100 and 128, respectively. These patient-specific (or mass customized) cutting guides 100 and 128 are designed to replace conventional resection tools by providing slots 108 and 136, respectively, that are contoured to the shape of prosthetic 82 and oriented to match the planned surgical cut as shown in FIGS. 9A and 9B and FIGS. 11A and 11B.

Figure 12A:
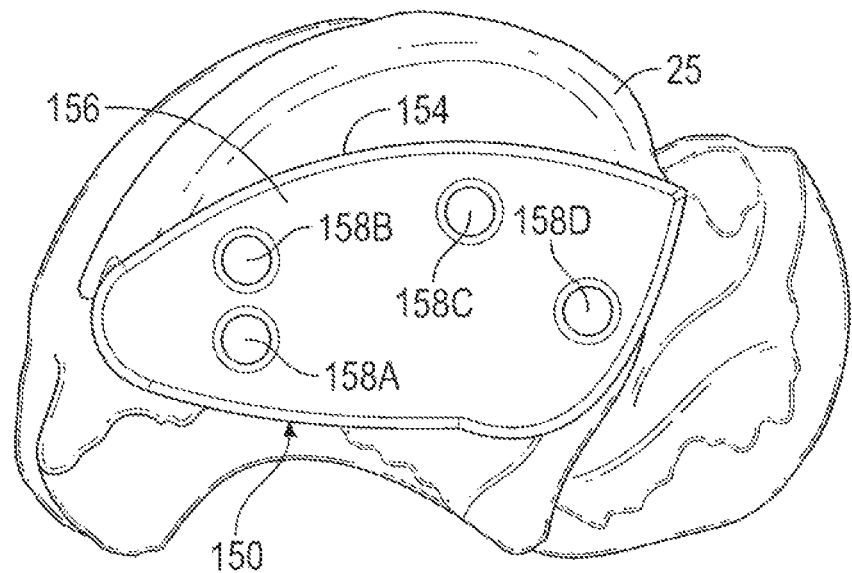
FIGS. 12A and 12B are lateral views of a talus and distal tibia, respectively, having mounted thereto patient-specific or mass customized cutting tool placement guides that includes screw hole guides for a lateral approach.
Figure 12B:
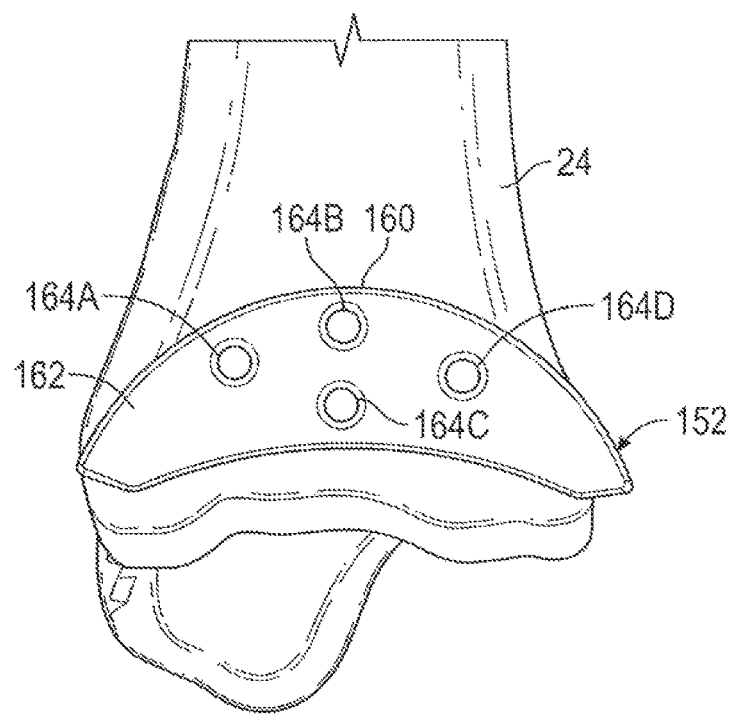

FIGS. 12A and 12B show patient-specific (or mass customized) cutting guides 150 and 152, respectively, for talus 25 and distal tibia 24, respectively, having predrilled holes 158A-158D and 164A-164D, respectively, that may be used to align conventional cutting instruments in the correct orientation.

Cutting guides 150 and 152 can have similar features as cutting guides 100 and 128 of FIGS. 9A and 9B and 11A and 11B, respectively, but without slots 108 and 136, respectively, and with different hole patterns. In particular, cutting guide 150 can include main body 154 having a patient-specific, or mass customized, bone-facing surface (not shown), guide surface 156 and pin holes 158A, 158B, 158C and 158D. The patient-specific surface can comprise an irregularly shaped surface having contours that closely match with or form a mirror image of highlighted area 120 of talus model 27, which will closely conform to the corresponding portion of talus 25 (FIGS. 3A and 3B). Main body 154 can be used to align pin holes 158A-158D with talus 25 and the subsequent insertion of guide pins into holes 158A-158D for use with conventional cutting guides, such as those described in U.S. Pub. No. 2004/0039394 to Conti et al. and U.S. Pub. No. 2014/0188236 to McGinley et al.

Cutting guide 152 can include main body 160 having a patient-specific, or mass customized, bone-facing surface (not shown), guide surface 162 and pin holes 164A, 164B, 164C and 164D. The patient-specific surface can comprise an irregularly shaped surface having contours that closely match with or form a mirror image of highlighted area 94 of tibia model 26, which will closely conform to the corresponding portion of tibia 24 (FIGS. 3A and 3B). Main body 160 can be used to align pin holes 164A-164D with tibia 24 and the subsequent insertion of guide pins into holes 164A-164D for use with the aforementioned conventional cutting guides.

FIG. 13 is a front view of tibia 24 and talus 25 having implanted therein conventional total ankle replacement prosthetic 170 via an anterior approach to total ankle replacement. Prosthetic 170 can include tibia component 172, talus component 174 and bearing component 176 disposed therebetween. Tibia component 172 is shaped to fit against resected surface 178 and medial malleolus 98 of tibia 24. Talus component 174 is shaped to fit against resected surface 179 of talus 25. Bearing component 176 can be coupled to tibia component 172 and can be shaped to slide along a mating surface of talus component 174.

Figure 14:
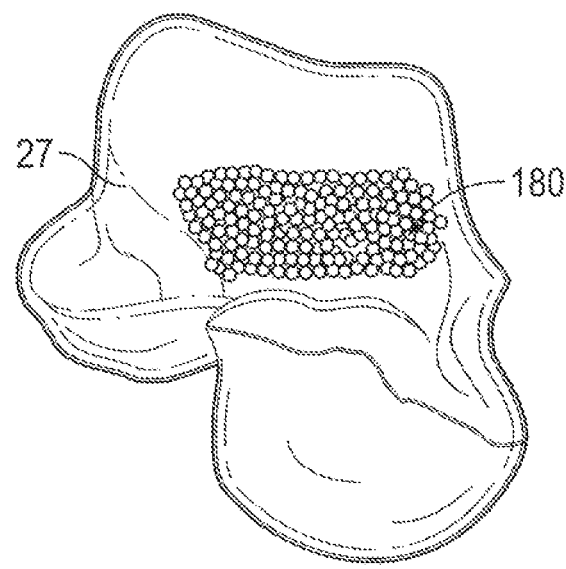
FIG. 14 is a superior view of a talus model showing surface points utilized to produce an anterior total ankle patient-specific talus cutting guide.
Figure 15:
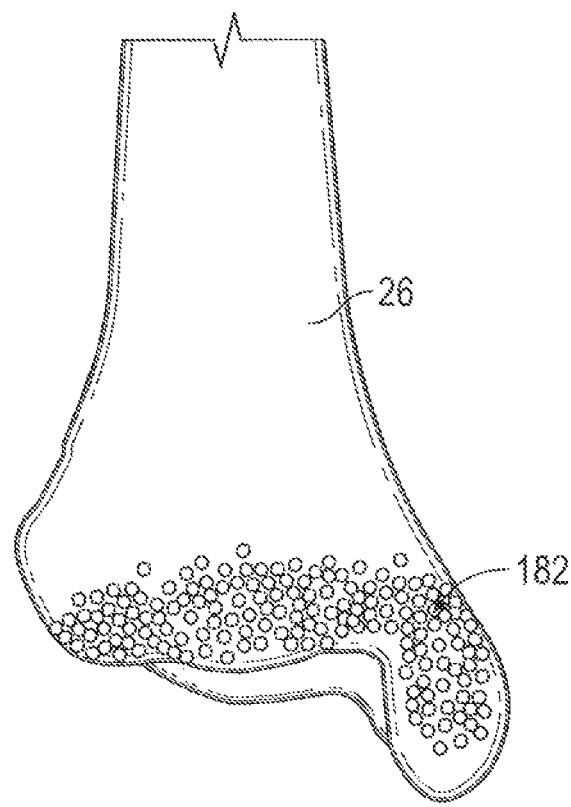
FIG. 15 is a front view of a distal tibia model showing surface points utilized to produce an anterior total ankle patient-specific tibia cutting guide.

FIG. 14 is a superior view of a talus model 27 showing surface points 180 utilized to produce an anterior total ankle patient-specific (or mass customized) talus cutting guide. Surface pints 180 can comprise surface features of talus model 27 on proximal and anterior surfaces of a proximal portion of talus 25. FIG. 15 is a front view of distal tibia model 26 showing surface points 182 utilized to produce an anterior total ankle patient-specific (or mass customized) tibia cutting guide. Surface pints 182 can comprise surface features of tibia model 26 on anterior and distal surfaces of a distal portion of tibia 24.

An anterior approach to total ankle arthroplasty involves performing a straight resection cut on the distal tibia surface, while protecting the medial malleolus 98 and a straight resection cut on the talus, as shown in FIG. 13. The anterior approach procedure can be made patient-specific by creating pin placement guides (FIGS. 17A-18B or FIGS. 19-22C) that will place pins (FIG. 23) later used to support resection guides (FIGS. 16A and 16B or FIGS. 24A-27E) with anatomy matching areas.

Figure 22A:
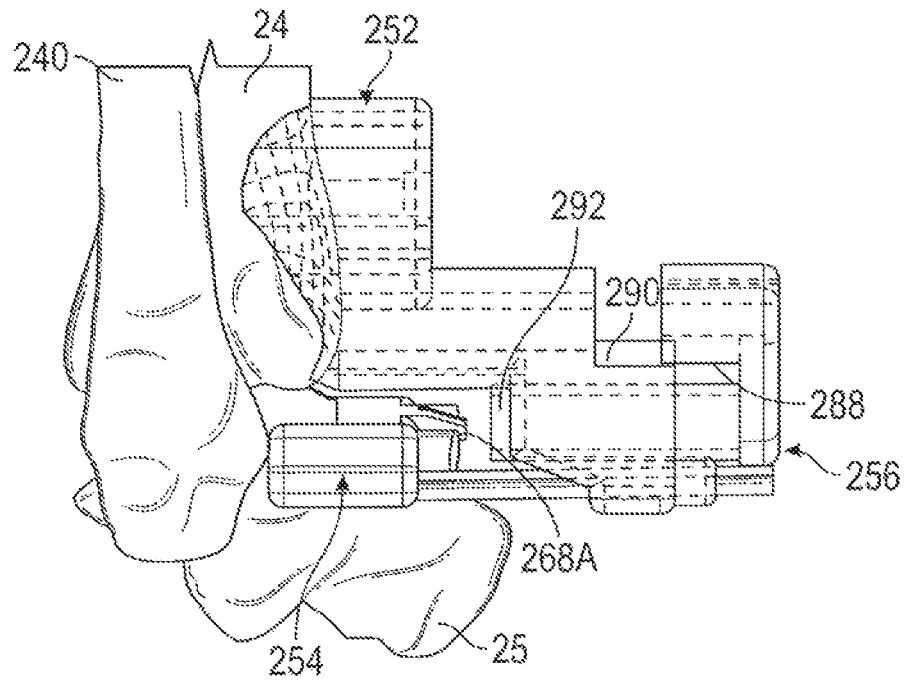
FIGS. 22A-22C are side views of the tibia, talus and fibula of FIG. 21 showing placement of the tibia pin guide and the talus faceplate with a progression of the interlocking component through the tibia pin guide to seat on the talus faceplate.
Figure 22B:
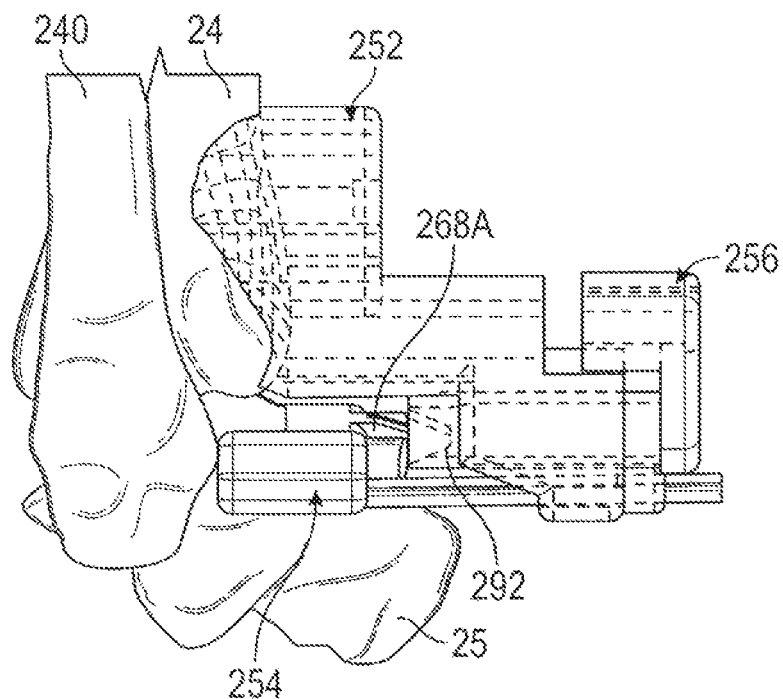
Figure 22C:
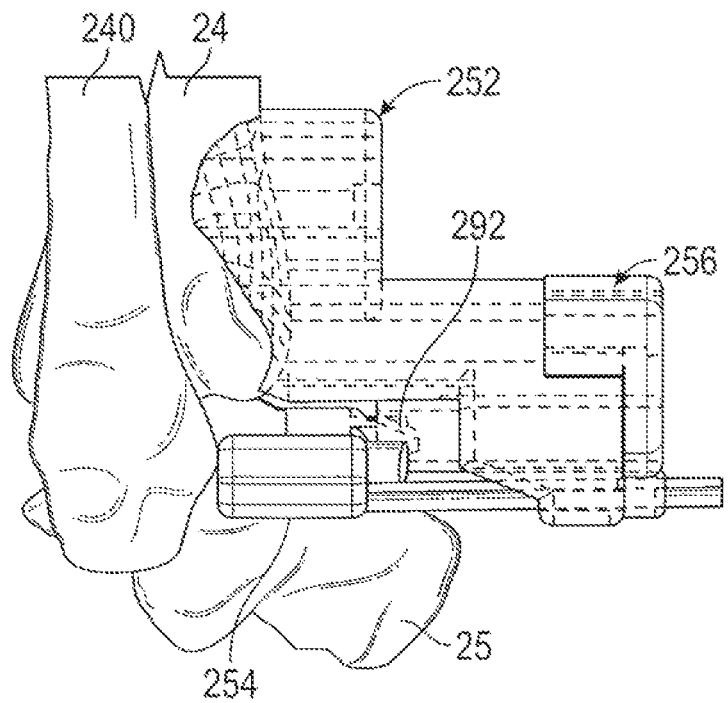
Figure 23:
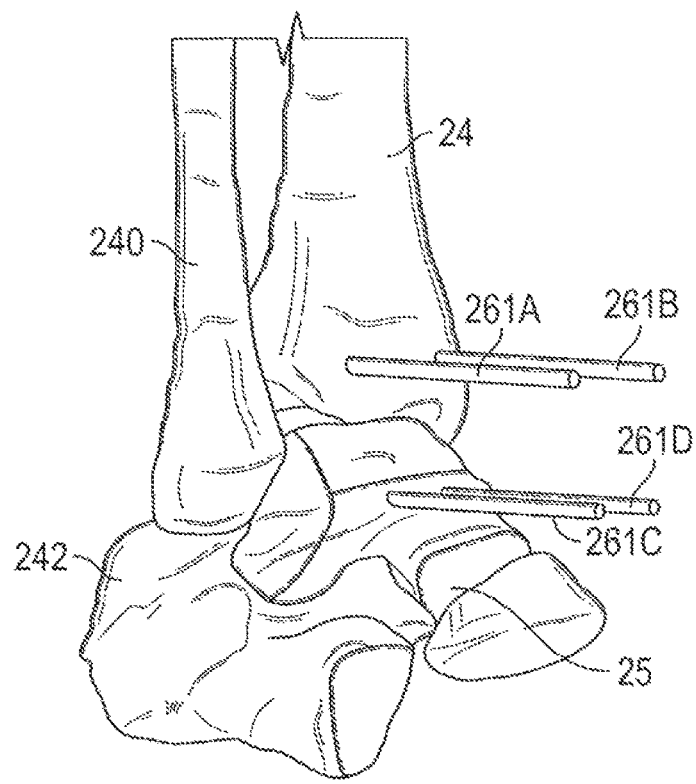
FIG. 23 is a perspective view of the tibia, talus, fibula and calcaneus of FIGS. 19-22C showing placement of two tibia pins and the two talus pins that are placed through the tibia pin guide after assembly of the three-part ankle pin guide.

Each patient-specific (or mass customized) pin placement guide (FIGS. 17A-18B [variant I] or FIGS. 19-22C [variant II]) can be designed to match those anatomically matched areas in order to position tibia and talus pins, illustrated in FIG. 23.

Each patient-specific (or mass customized) cutting guide (FIGS. 16A and 16B [variant I] or FIGS. 24A-27E [variant II]) can be designed to match those anatomically matched areas, which are then used to provide location for predrilled holes on both the tibia and talus that may be used to place the distal tibia and proximal talus cutting blocks.

Figure 16A:
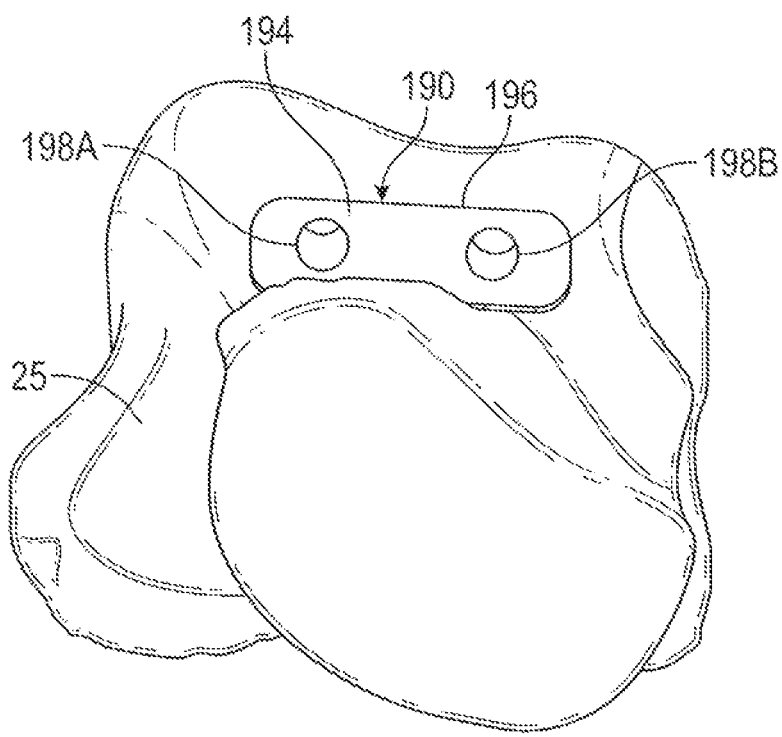
FIGS. 16A and 16B are anterior views a talus and tibia showing placement of talus and tibia cutting guides, respectively, for a total ankle patient-specific procedure for an anterior approach.
Figure 16B:
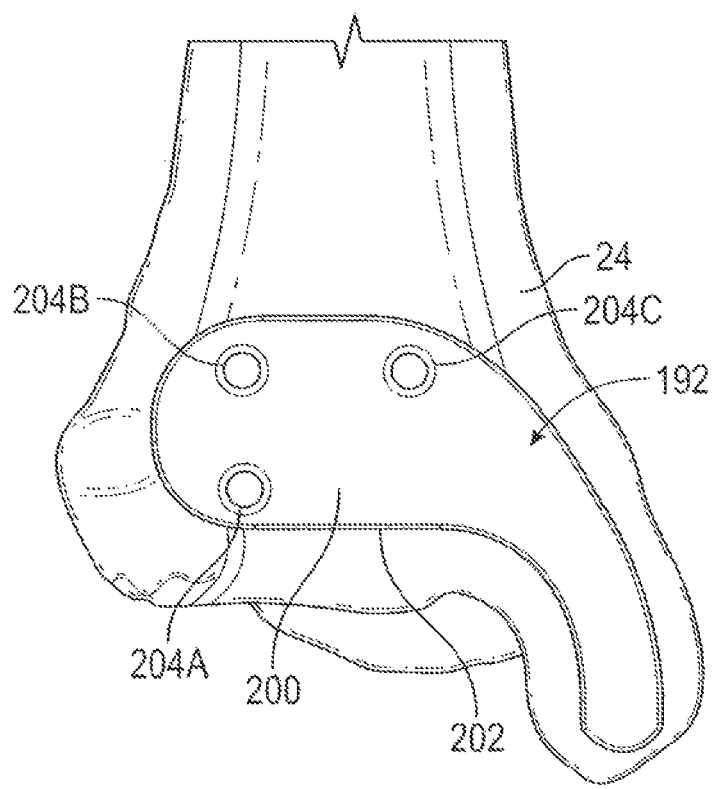

FIGS. 16A and 16B are anterior views of talus 25 and tibia 24 showing placement of talus and tibial cutting guides 190 and 192, respectively, for a total ankle patient-specific procedure.

Cutting guide 190 can include main body 194 having a patient-specific, or mass customized, bone-facing surface (not shown), guide surface 196 and pin holes 198A and 198B. The patient-specific surface can comprise an irregularly shaped surface having contours that closely match with or form a mirror image of surface points 180 of talus model 27 (FIG. 15A), which will closely conform to the corresponding portion of talus 25 (FIGS. 3A and 3B). Main body 194 can be used to align pin holes 198A and 158B with talus 25 and the subsequent insertion of guide pins into holes 168A and 168B for use with the aforementioned conventional cutting guides.

Cutting guide 192 can include main body 200 having a patient-specific, or mass customized, bone-facing surface (not shown), guide surface 202 and pin holes 204A, 204B and 204C. The patient-specific surface can comprise an irregularly shaped surface having contours that closely match with or form a mirror image of surface points 182 of tibia model 26, which will closely conform to the corresponding portion of tibia 24 (FIGS. 3A and 3B). Main body 200 can be used to align pin holes 204A-204C with tibia 24 and the subsequent insertion of guide pins into holes 204A-204C for use with the aforementioned conventional cutting guides.

Figure 17A:
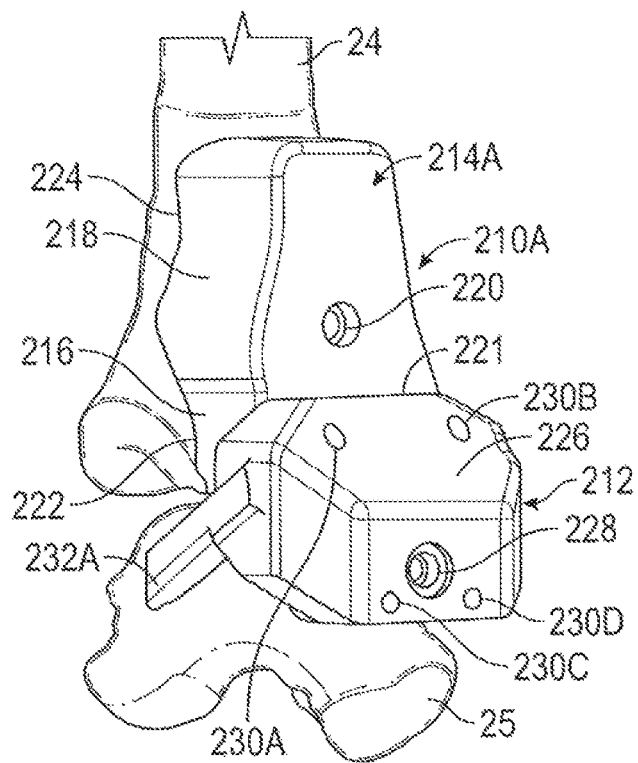
FIGS. 17A and 17B are perspective views of a tibia and talus showing placement of enhanced referencing and standard referencing, interlocking, two-part talus and tibia pin guides, respectively, for total ankle patient-specific procedures.
Figure 17B:
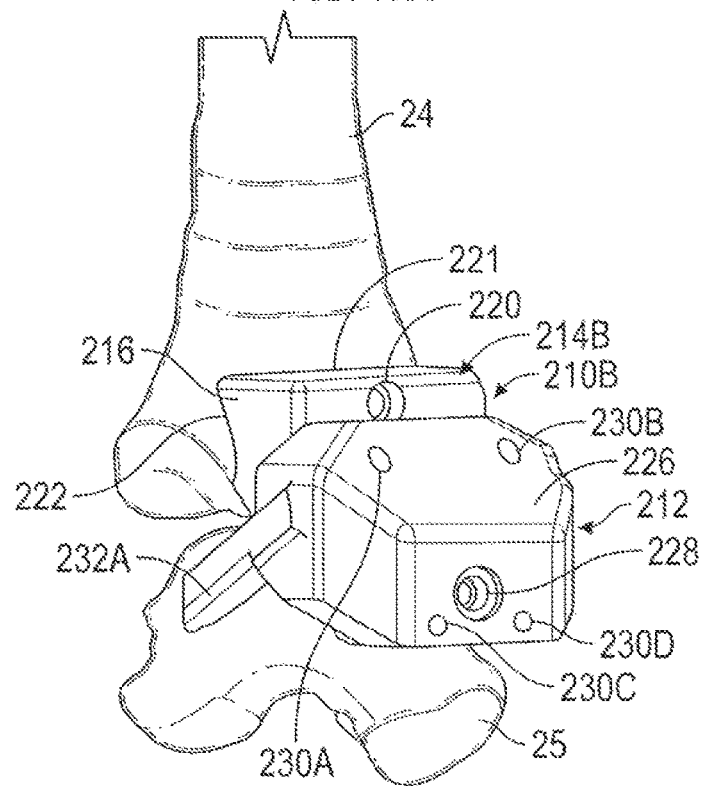

FIGS. 17A and 17B are perspective views of tibia 24 and talus 25 showing placement of enhanced referencing and standard referencing, interlocking, two-part talus and tibia pin guides 210A and 210B, respectively, for total ankle patient-specific procedures. Enhanced referencing pin guide 210A includes talus guide 212 and enhanced tibia guide 214A. Standard referencing pin guide 210B include talus guide 212 and standard tibia guide 214B. Enhanced tibia guide 214A can include main body 216 and extension 218, while standard tibia guide 214B can include main body 216 without extension 218.

Tibia guide 214A can include mounting bore 220, front surface 221 and patient-specific surface 222 at main body 216 and patient-specific surface 224 at extension 218. Patient-specific surface 222 can comprise an irregularly shaped surface having contours that closely match with or form a mirror image of surface points 182 of tibia model 26, which will closely conform to the corresponding portion of tibia 24 (FIGS. 3A and 3B). Patient-specific surface 224 can comprise an irregularly shaped surface having contours that closely match with or form a mirror image of anterior surfaces of tibia model 26 proximal of surface points 182, which will closely conform to the corresponding portions of tibia 24 (FIGS. 3A and 3B).

Tibia guide 214A or tibia guide 214B can be positioned against the anterior surface of tibia 24 and nestled into place against the contours of tibia 24. Thereafter, a fastener can be inserted into mounting bore 220 to secure tibia guide 214A or 214B to tibia 24.

FIGS. 18A and 18B are perspective and superior views of talus 25 showing placement and anatomical contacts of talus guide 212. Talus guide 212 can include main body 226, mounting bore 228, rear surface 229, pin holes 230A, 230B, 230C and 230D and extensions 232A and 232B. Extensions 232A and 232B can include patient-specific surfaces 234A and 234B, respectively. Patient-specific surfaces 234A and 234B can comprise irregularly shaped surfaces having contours that closely match with or form mirror images of surfaces of talus 25 or talus model 27, while rear surface 229 lies flush with front surface 221 of tibia guide 214A or 214B. Positioned as such pin holes 230A and 230B can align with pin holes (not shown) in main body 216 of tibia guide 214A or 214B. Pins can be inserted into pin holes 230A and 230B and into the tibia guide pin holes (not shown) to ensure alignment, and subsequently a fastener can be inserted into mounting bore 228 to secure talus guide 212 to talus 25. After both tibia guide 214A or 214B and talus guide 212 are secured with fasteners at mounting bores 220 and 228, respectively, pins can be removed from pin holes 230A and 230B and pin holes can be drilled into tibia 24 at pin holes 230A and 230B and pin holes can be drilled into talus 25 at pin holes 230C and 230D. Pins (e.g., pins 261A-261D of FIG. 23) can be inserted into the drilled pin holes and a cutting guide(s) (e.g., cutting guides 300 and 350 of FIGS. 24A-27E) can be used to form resections on tibia 24 and talus 25. Pins 261A-261D of FIG. 23 can alternatively be placed into tibia 24 and talus 25 using the pin guide of FIGS. 19-22C.

Figure 19:
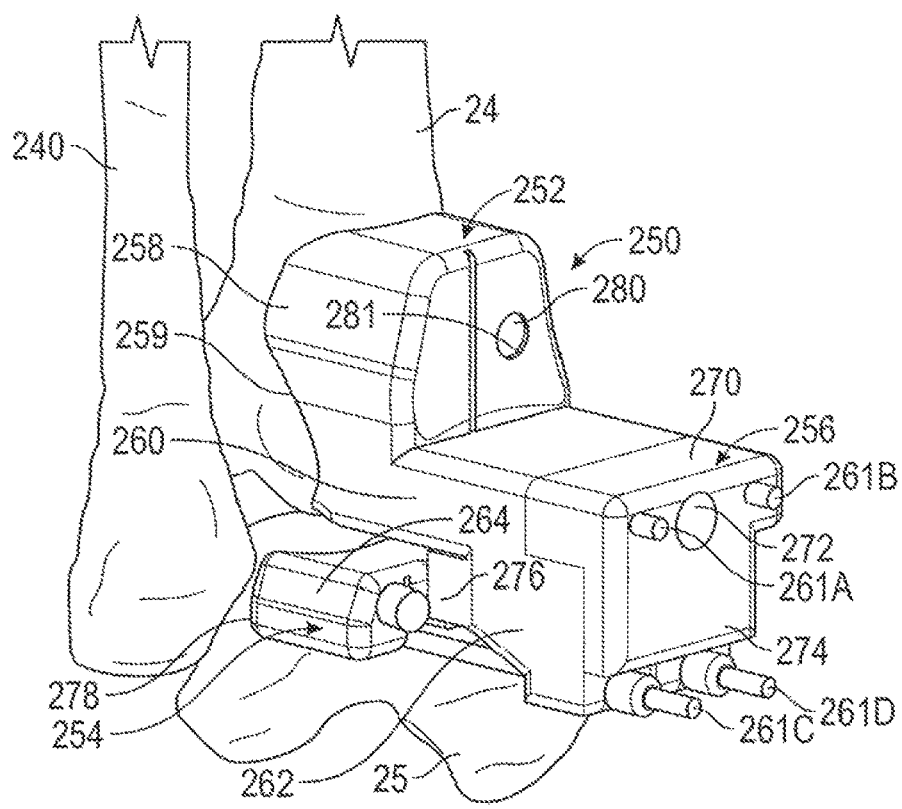
FIG. 19 is a perspective view of a tibia, talus and fibula showing placement of an interlocking three-part ankle pin guide having a talus faceplate, tibia pin guide and interlocking component.
Figure 20:
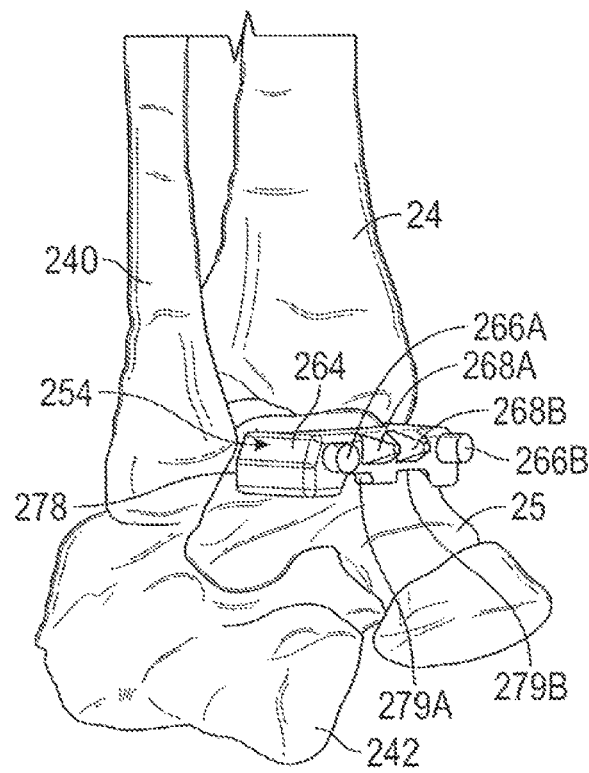
FIG. 20 is a perspective view of the tibia, talus and fibula of FIG. 19 and a calcaneus showing placement of a talus faceplate and associated placement pins.

FIG. 19 is a perspective view of tibia 24, talus 25 and fibula 240 showing placement of interlocking three-part ankle pin guide 250. Three-part ankle pin guide 250 can include tibia pin guide 252, talus faceplate 254 and interlocking component 256. Tibia pin guide 252 can include patient-specific extension 258, patient-specific surface 259, pin guide body 260, pins 261A-261D and window body 262. Pin guide body 260 can extends away from patient-specific extension 258 at an edge of patient-specific surface 259. As shown in FIG. 20, talus faceplate 254 can include main body 264, fasteners 266A and 266B and posts 268A and 268B. Interlocking component 256 can include pin body 270, fastener 272, extension 274 and lock 276.

FIG. 20 is a perspective view of the tibia 24, talus 25 and fibula 240 of FIG. 19 and calcaneus 242 showing placement of talus faceplate 254 and associated placement fasteners 266A and 266B. Talus faceplate 254 can include patient-specific surface 278 that can comprise an irregularly shaped surface having contours that closely match with or form a mirror image of surface points 180 of talus model 27, which will closely conform to the corresponding portion of talus 25. Talus faceplate 254 allows for independent control over the level of contact with talus 25 without regard to tibia pin guide 252. Talus faceplate 254 has a low profile, i.e., is close to talus 25, so that interference with placement of tibia pin guide 252 is reduced.

After patient-specific surface 278 is firmly seated, fasteners 266A and 266B can be inserted into corresponding pin holes in talus faceplate 254 to secure talus faceplate 254 to talus 25. Talus faceplate 254 can also include openings, holes or recesses, 279A and 279B that allow guide pins 261C and 261D to pass underneath or through talus faceplate 254 to engage talus 25. Posts 268A and 268B extend from talus faceplate 254 and provide engagement or locking features that allow lock 276 of interlocking component 256 to connect to talus faceplate 254. In an example, posts 268A and 268B have center axes that extend parallel to the pin holes for fasteners 266A and 266B.

Figure 21:
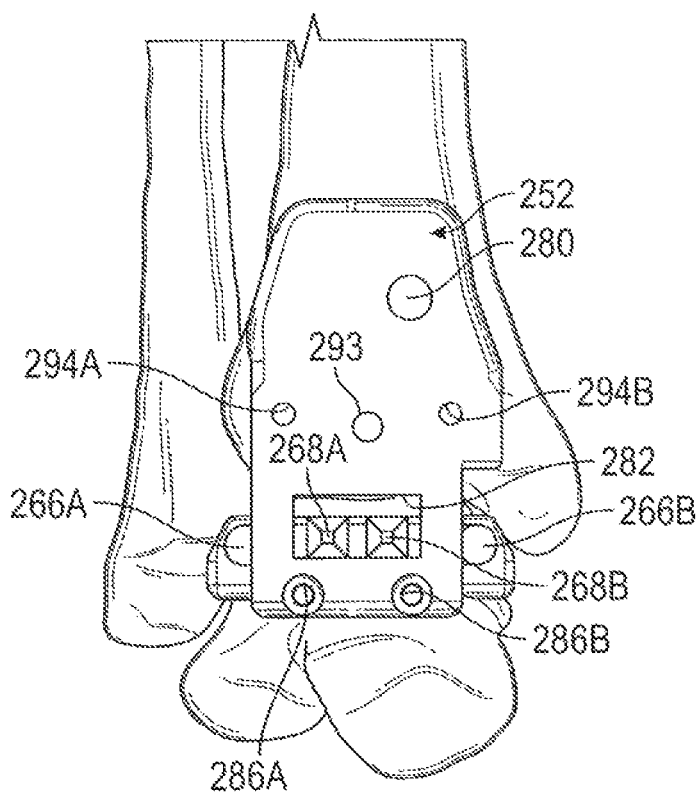
FIG. 21 is a perspective view of the tibia, talus and fibula of FIG. 20 showing placement of a tibia pin guide looking through a slot that in the tibia pin guide to view the talus faceplate.

FIG. 21 is a perspective view of tibia 24, talus 25 and fibula 240 of FIG. 20 showing placement tibia pin guide 252 and talus faceplate 254. Patient-specific surface 259 of patient-specific extension 258 can be seated onto tibia 24 to properly orient tibia pin guide 252. Patient-specific surface 259 can comprise an irregularly shaped surface having contours that closely match with or form a mirror image of surface points 182 of tibia model 26, which will closely conform to the corresponding portion of tibia 24. Pins 261A and 261B can be inserted into pin guide body 260 at pin holes 294A and 294B. Fastener 280 can be inserted into a corresponding bore 281 in patient-specific extension 258 to secure tibia pin guide 252 to tibia 24. The ankle of the patient can be adjusted by moving the foot of the patient through flexion until posts 268A and 268B are visible through window, or socket, 282 in window body 262 of tibia pin guide 252. Thus, bores 286A and 286B can be aligned with openings 279A and 279B (FIG. 20), respectively, in talus faceplate 254. Pins 261C and 261D can be inserted into bores 268A and 268B and openings 279A and 279B to link tibia pin guide 252 and talus faceplate 254.

FIGS. 22A-22C are side views of tibia 24, talus 25 and fibula 240 of FIG. 21 showing placement of tibia pin guide 252 and talus faceplate 254 with a progression of interlocking component 256 being inserted into window 282 of tibia pin guide 252 from an extended position to a position seated on the faceplate 254.

As can be seen in FIG. 22A, lock 276 can be inserted into window 282 so that bottom surface 288 of pin body 270 aligns with top surface 290 of window body 262. Thus, lock 276 and ping body 270 form a U-shaped structure with extension 274. Top surface 290 thus forms a shelf upon which bottom surface 288 can rest. Positioned as such, extension 274 will oppose window body 262. As shown in FIG. 22B, interlocking component 256 can be advanced toward talus faceplate 254 so that bottom surface 288 slides along top surface 290. As shown in phantom in FIGS. 22A-22C, lock 276 can include alignment sockets 292 that can be configured to mate with and receive posts 268A and 268B. Posts 268A and 268B can be configured to tightly lock tibia pin guide 252 and talus faceplate 254 into rotational alignment. For example, posts 268A and 268B can be pyramid-type bodies that have four planar surfaces facing four orthogonal directions (e.g., superior, lateral, inferior and medial). Alignment sockets 292 can have corresponding planar surfaces that mate flush with the four planar pyramid surfaces thereby ensuring alignment of tibia pin guide 252 with talus faceplate 254. As shown in FIG. 22C, after interlocking component 256 is fully engaged with talus faceplate 254, fastener 272 (FIG. 19) can be inserted into bore 293 (FIG. 21) of interlocking component 256 to secure interlocking component 256 into place with tibia pin guide 252. Thereafter, pins 261A and 261B can be inserted into interlocking device 256 at interlocking bores (not shown), respectively, of tibia pin guide 252. After pins 261A-261D are inserted into fully assembled interlocking three-part ankle pin guide 250, interlocking component 256, tibia pin guide 252 and talus faceplate 254 can be removed from pins 261A-261D, as shown in FIG. 23.

FIG. 23 is a perspective view of tibia 24, talus 25, fibula 240 and calcaneus 242 of FIGS. 19-22C showing placement of two tibia pins 261A and 261B and two talus pins 261C and 261D that have been placed through tibia pin guide 252 after assembly of three-part ankle pin guide 250. As such, tibia 24 and talus 25 are prepared for receiving a cutting guide via pins 261A-261D, as discussed with reference to FIGS. 24A-27E.

FIGS. 24A-24D are various views of tibia 24, talus 25 and fibula 240 coupled to talus cutting guide 300, which can be fit onto pins 261A-261D of FIG. 23. As discussed, pins 261A-261D can be placed by three-part ankle pin guide 250 of FIGS. 19-22C. FIGS. 24A-24D are discussed concurrently. Talus cutting guide 300 can include main body 302, extension 304, cutting body 306, pin flange 308, window 310 and cutting slot 312.

Figure 24A:
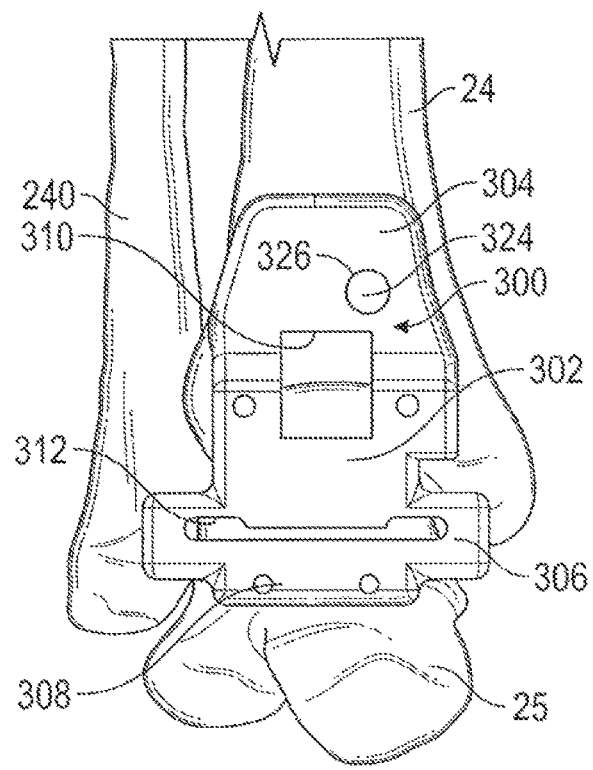
FIGS. 24A-24D are various views of a tibia, talus and fibula coupled to a talus cutting guide that can be fit on the pins of FIG. 23 placed by the three-part ankle pin guide of FIGS. 19-22C.
Figure 24B:
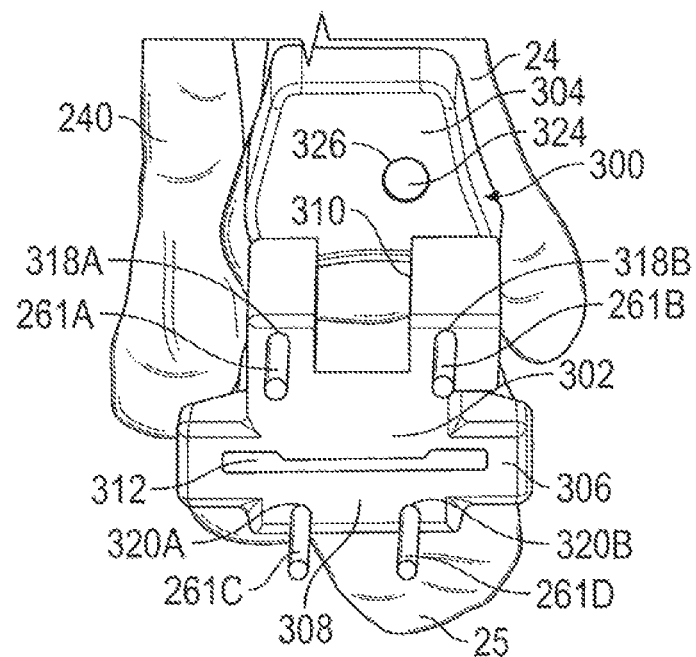
Figure 24C:
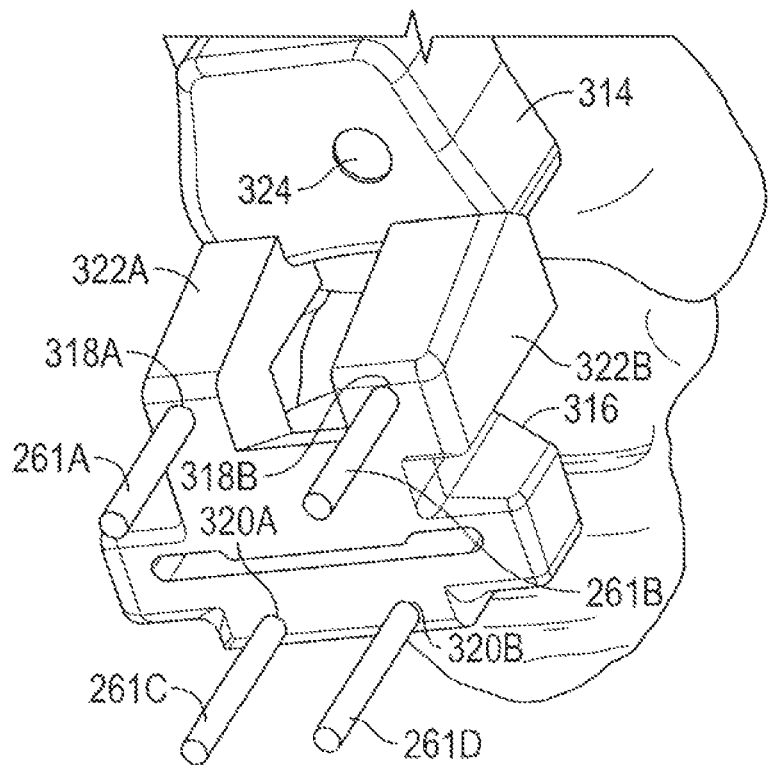
Figure 24D:
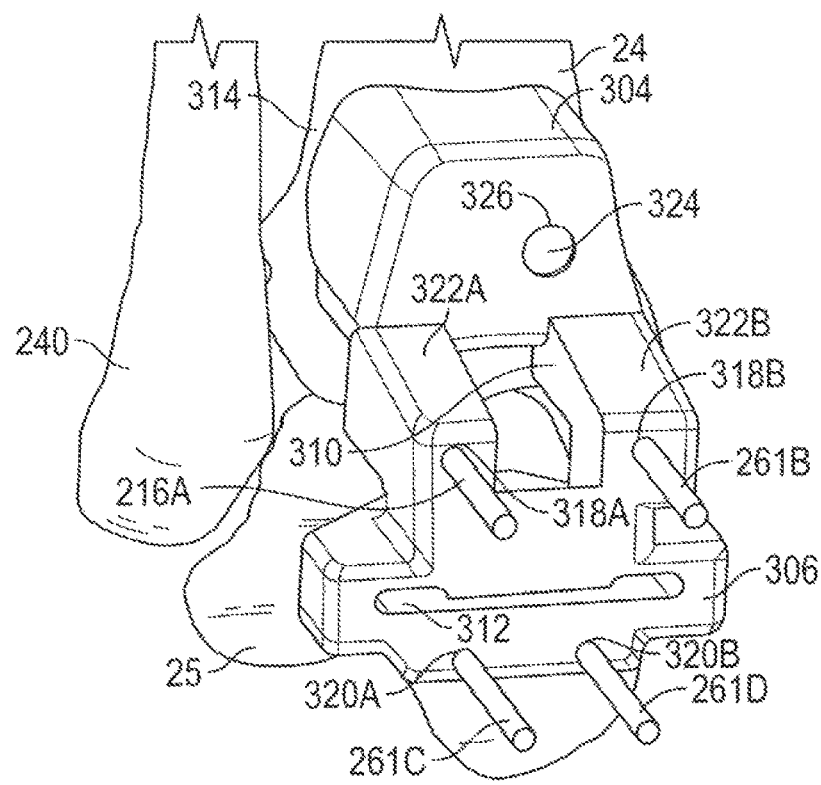

As shown in FIGS. 24C and 24D, extension 304 and cutting body 306 can include patient-specific surfaces 314 and 316, respectively. Patient-specific surfaces 314 and 316 can be shaped to closely conform to or be mirror images of surface points 182 and 180, respectively, of tibia and talus models 26 and 27.

In particular, patient-specific surface 314 can comprise an irregularly shaped surface having contours that closely match with or form a mirror image of surface points 182 of tibia model 26, which will closely conform to the corresponding portion of tibia 24, and patient-specific surface 316 can comprise an irregularly shaped surface having contours that closely match with or form a mirror image of surface points 180 of talus model 27, which will closely conform to the corresponding portion of talus 25.

Extension 304 can include pin holes 318A and 318B to receive pins 261A and 261B. Cutting body 306 can include pin holes 320A and 320B to receive pins 261C and 261D. As such, extension 304 and cutting body 306 can be slid onto and over pins 261A-261D until patient-specific surfaces 314 and 316 engage tibia 24 and talus 25. Main body 320 can include beams 322A and 322B that position cutting body 306 in the anterior direction relative to extension 304 to allow cutting body 306 to be positioned anteriorly of talus 25. As such, beams 322A and 322B offset cutting body 306 from extension 304.

Fastener 324 can be inserted into fastener bore 326 in extension 304 to secure talus cutting guide 300 to tibia 24. As such, cutting slot 312 is positioned over the desired area of talus 25 to be resected. In an example, cutting slot 312 can be positioned to from a planar resection along talus 25 parallel to or substantially parallel to a transverse plane through talus 25, the planar resection extending though the portion of talus 25 above the corresponding location of surface points 180. Thus, a cutting tool, such as a saw, can be inserted into cutting slot 312 with or without the aid of guide pins 261A-261D to perform the resection. Window 310 in main body 302 allows the surgeon to view the portion of talus 25 to be resected during the resectioning procedure.

Figure 25:
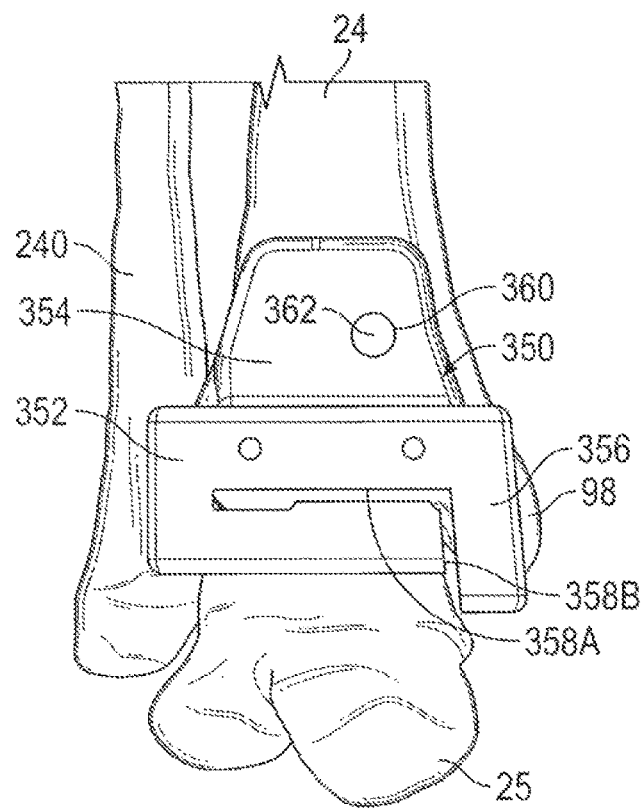
FIG. 25 is a front view of a tibia, talus and fibula coupled to a tibia cutting guide that is can be fit on the pins of FIG. 23 placed by the three-part ankle pin guide shown in FIGS. 19-22C.

FIG. 25 is a front view tibia 24, talus 25 and fibula 240 coupled to tibia cutting guide 350, which can be fit on the pins 261A-261D of FIG. 23. Pins 261A-261D can be placed by the three-part ankle pin guide 250 of FIGS. 19-22C. Tibia cutting guide 350 can include main body 352, extension 354, medial malleolus flange 356, first cutting slot 358A and second cutting slot 358B.

Extension 354 can include patient-specific surface (not shown), which can comprise an irregularly shaped surface having contours that closely match with or form a mirror image of surface points 182 of tibia model 26, which will closely conform to the corresponding portion of tibia 24.

Extension 354 can include fastener bore 360, fastener 362 and pin holes 364A and 364B. Pin holes 364A and 364B can receive pins 261A and 261B. As such, extension 354 can be slid onto and over pins 261A and 261B until the patient-specific surface of extension 354 engages tibia 24. Extension 354 can be nestled into position against tibia 24 and fastener 362 can be inserted into bore 360 to secure tibia cutting guide 350 against tibia 24. As such, cutting slots 358A and 358B can be positioned over the desired area of tibia 24 to be resected. In an example, cutting slot 358A can be positioned to form a planar resection along tibia 25 parallel to or substantially parallel to a transverse plane through tibia 24, the planar resection extending though the portion of tibia 24 along the corresponding location of surface points 182. In an example, cutting slot 358B can be positioned to form a planar resection along medial malleolus 98 that can be parallel to or nearly parallel to a sagittal plane through tibia 24. Thus, a cutting tool, such as a saw, can be inserted into cutting slots 358A and 358B with or without the aid of guide pins 261A-261D to perform the resections. In an example, medial malleolus 98 can be resected first.

FIG. 26A-26E are anterior views of talus cutting guide 300 and tibia cutting guide 350 of FIGS. 24A-25 used sequentially to perform talus and tibia resections. In FIGS. 26A-26E, the talus resection is performed first and the tibia resection is performed second.

Figure 26A:
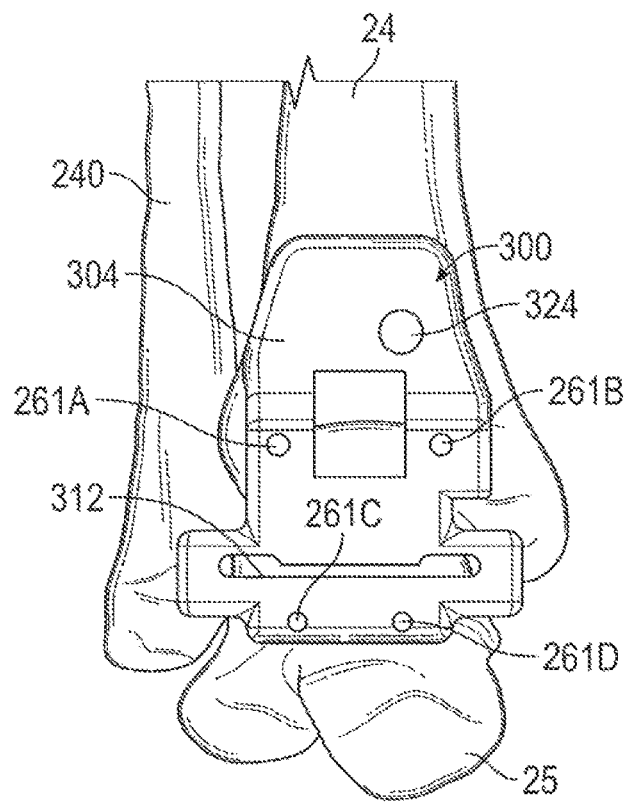
FIG. 26A-26E are anterior views of the talus cutting guide and tibia cutting guide of FIGS. 24A-25 positioned sequentially to perform talus and tibia resections.
Figure 26B:
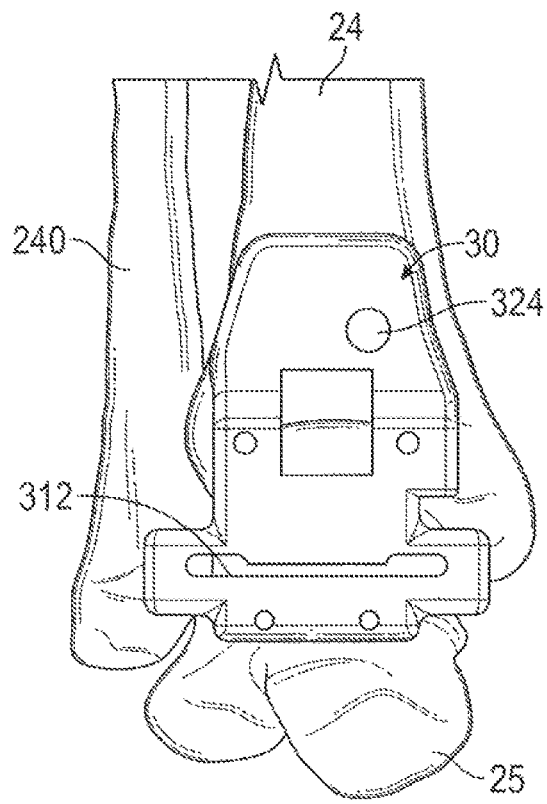

As shown in FIG. 26A, talus cutting guide 300 can be slit onto pins 261A-261D to ensure alignment of cutting slot 312 along the desired portion of talus 25. Fastener 324 can be inserted through extension 304 to secure cutting guide 300 to tibia 24. Coupling with pins 261A-261D can ensure that talus 25 is positioned in the desired orientation relative to tibia 24 to perform the resection. Next, as shown in FIG. 26B, a cutting instrument can be inserted into cutting slot 312 to remove the desired portion of talus 25. Subsequently, fastener 324 can be removed and cutting guide 300 can be slid off of pins 261A-261D.

Figure 26C:
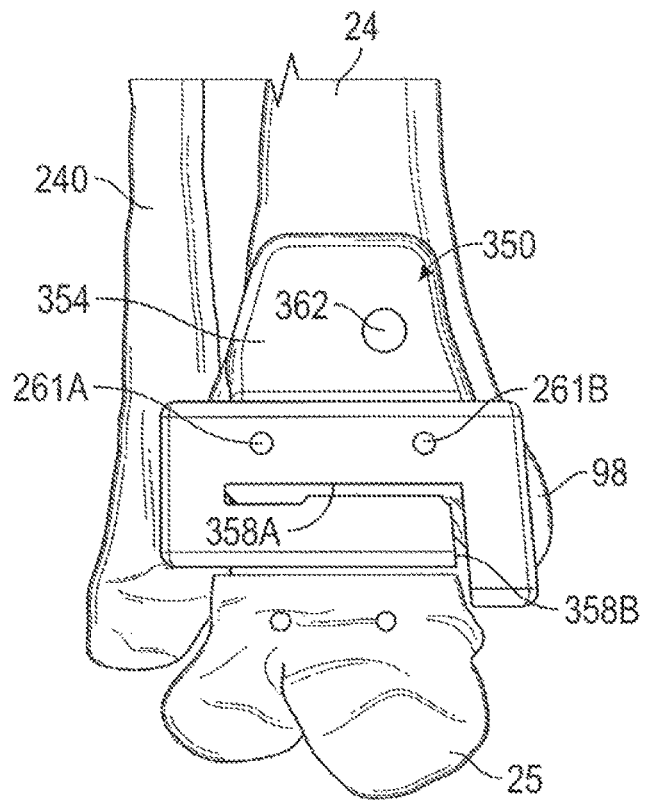
Figure 26D:
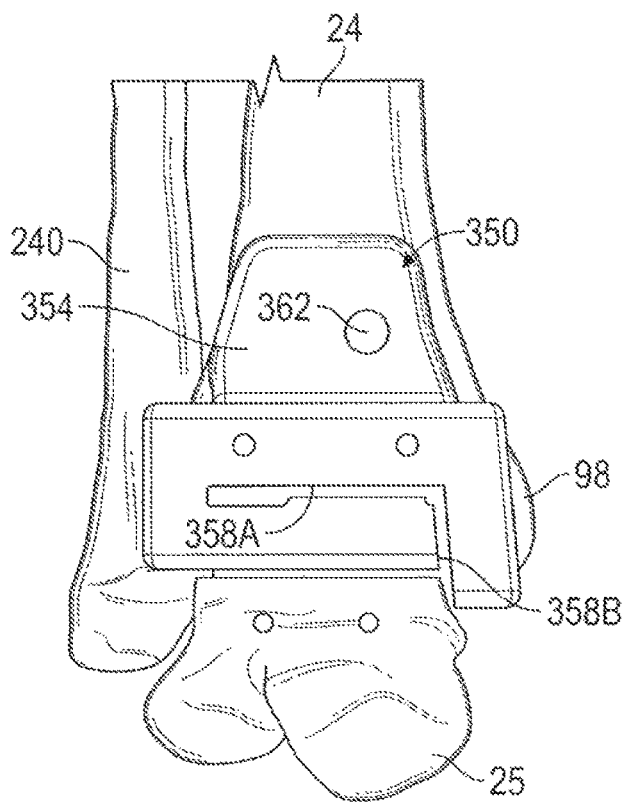

As shown in FIG. 26C, tibia cutting guide 350 can be slid onto pins 261A and 261 to ensure alignment of cutting slots 358A and 358B along the desired portions of tibia 24. Pins 261C and 261D can be removed from talus 25. Fastener 362 can be inserted through extension 354 to secure cutting guide 350 to tibia 24. Next, as shown in FIG. 26D, a cutting instrument can be inserted into cutting slot 358B to first remove a portion of medial malleolus 98. The cutting instrument can next be inserted into cutting slot 358A to secondly remove a portion of distal most surface 96 (FIG. 8) of tibia 24. Subsequently, fastener 362 can be removed and cutting guide 350 can be slid off of pins 261A and 261B.

Figure 26E:
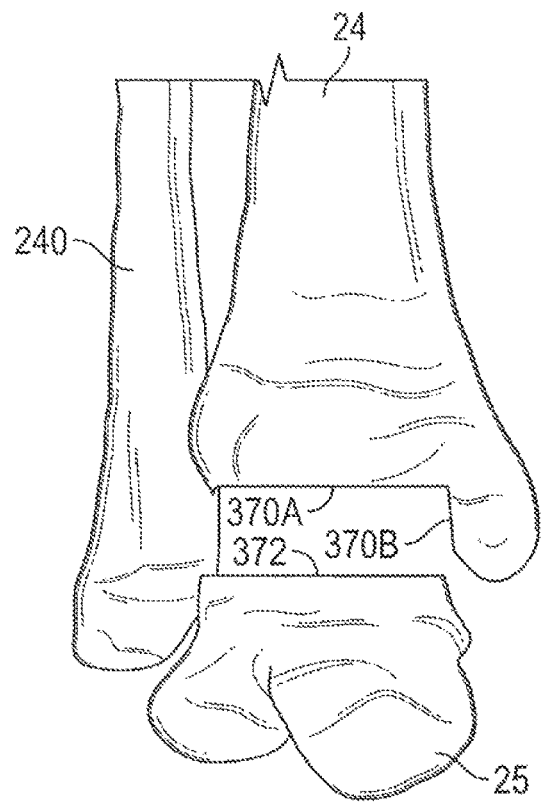
Figure 27A:
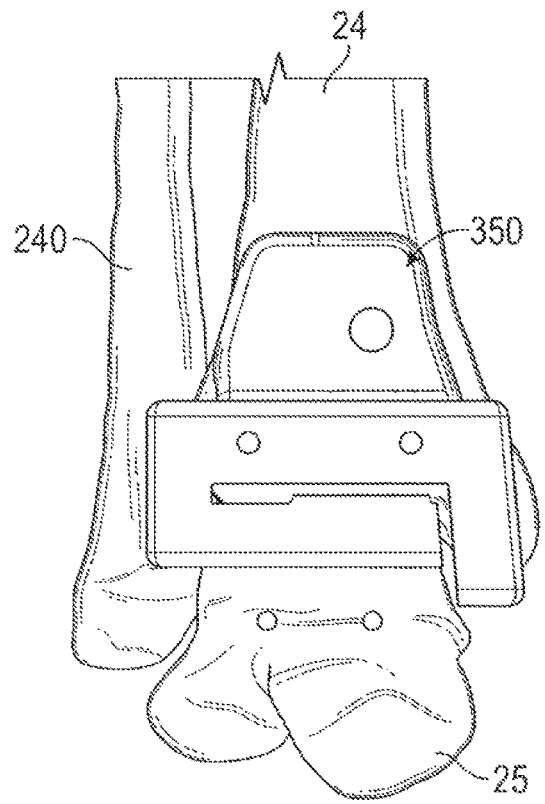
FIG. 27A-27E are anterior views of the tibia cutting guide and talus cutting guide of FIGS. 24A-25 positioned sequentially to perform talus and tibia resections.
Figure 27B:
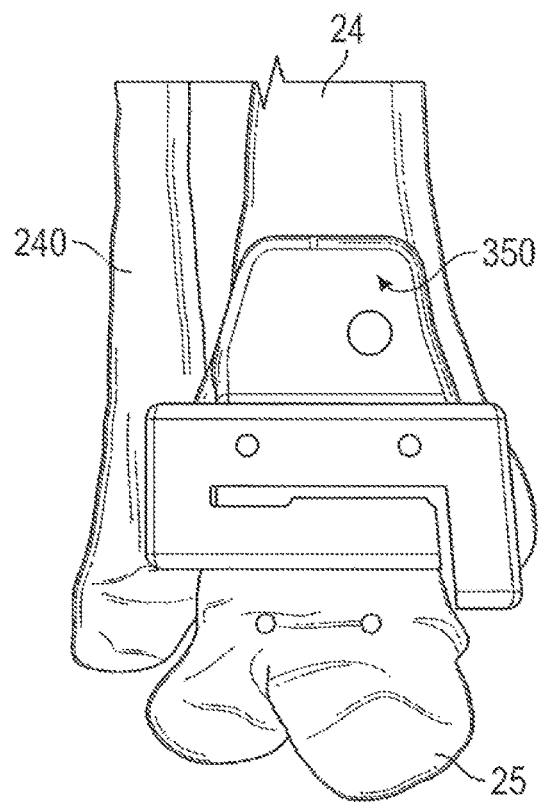
Figure 27C:
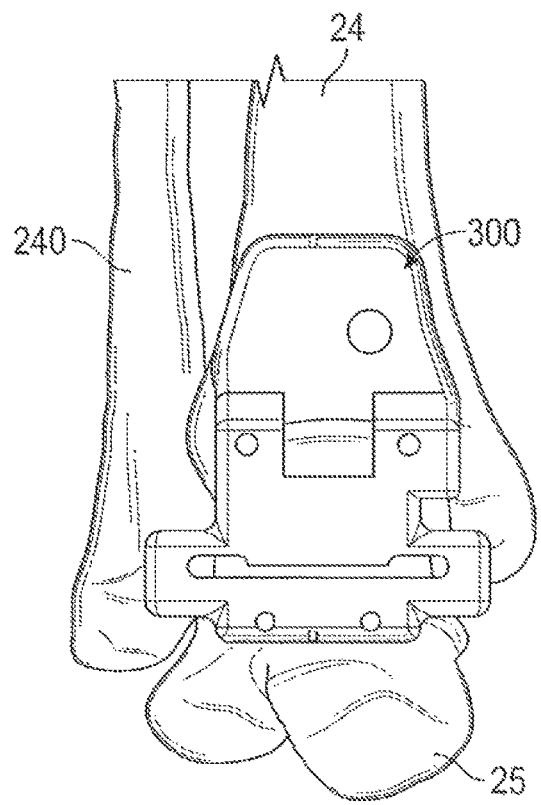
Figure 27D:
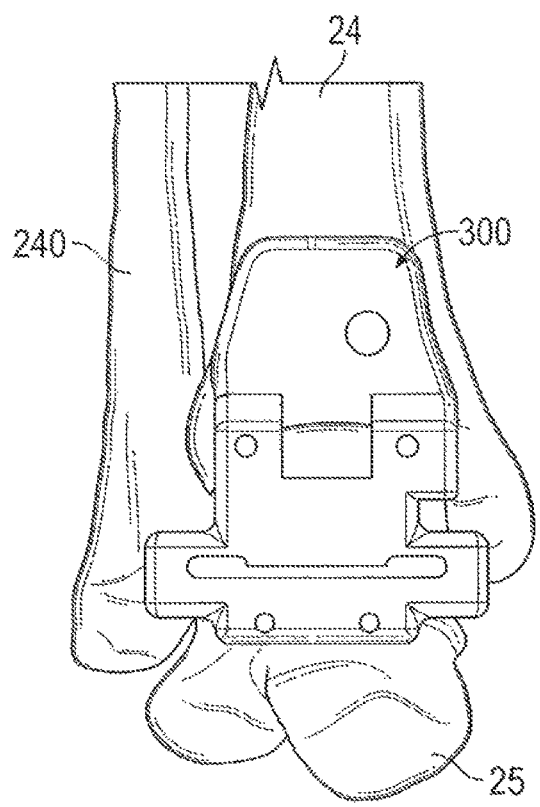
Figure 27E:
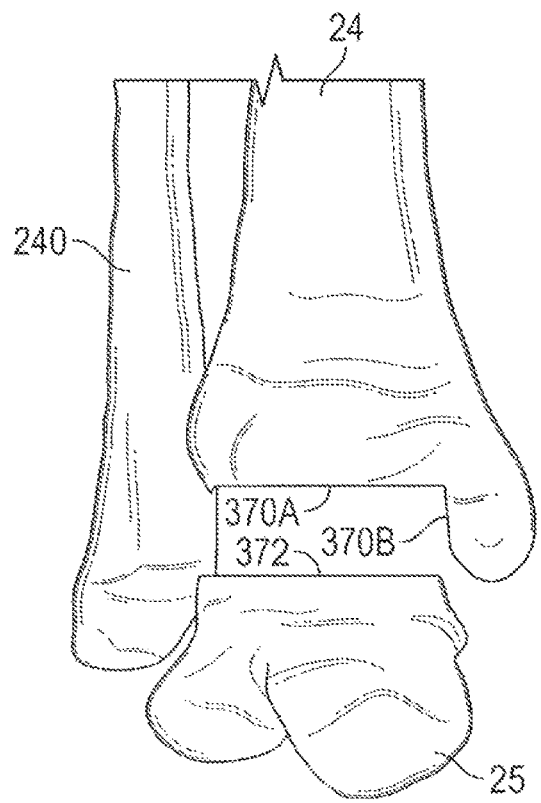

As shown in FIG. 26E, tibia 24 can be provided with resections 370A and 370B, and talus 25 can be provided with resection 372 as a result of performing resections with cutting slots 358A, 358B and 312. As shown, resection 370A can be a planar cut from the anterior surface of tibia 24 through to the anterior surface of tibia 24. Resection 370a can extend from the lateral surface of tibia 24 to medial malleolus 98. Resection 370B can be planar cut from the anterior surface of medial malleolus 98 through to the anterior surface of medial malleolus 98. Resection 370B can extend from the inferior surface of medial malleolus 98 up to resection 370A. Resection 372 can be a planar cut from the anterior surface of talus 25 through to the anterior surface of talus 25. Resection 372 can extend from the lateral surface of tibia 24 to the medial surface of talus 25. As such, tibia 24 and talus 25 can be fit with a total ankle replacement prosthetic device, similar to the one shown in FIG. 13.

FIG. 27A-27E are anterior views of tibia cutting guide 350 and talus cutting guide 300 of FIGS. 24A-25 used sequentially to perform talus and tibia resections. In FIGS. 27A-27E, the talus resection is performed first and the tibia resection is performed second. The procedures for performing the resections with respect to FIGS. 27A-27E are the same as those for FIGS. 26A-26E, except tibia cutting guide 350 is used to perform the tibia resection before talus cutting guide 300 is used to perform the talus resection.

The pin guides and cutting guides disclosed herein can provide advantages over conventional total ankle replacement arthroplasty procedures. For example, interlocking three-part ankle pin guide 250 can be fully adjustable in referencing off of the tibia for placement of tibia and talus pin guides 252 and 254. Interlocking component 256 can adjust the locking of pin guides 252 and 254 controlling contact with the joint line between the tibia and the talus. Pin guides 252 and 254 can be adjusted relative to each other inside the incision. Interlocking three-part ankle pin guide 250 can also allow talus pin guide 254 contact with the talus to be optimized independent of the tibia pin guide 252, can allow a surgeon to place talus pin guide 254 in contact with the talus without the tibia pin guide 252 blocking visibility, and can increase the stability of the joined guides 252 and 254, such as by use of multiple pins and fasteners and interlocking component 256.

VARIOUS NOTES & EXAMPLES

Example 1 can include or use subject matter such as a patient-specific pin guide for performing a total ankle arthroplasty, the patient-specific pin guide can comprise: a tibia pin guide that can comprise: a first patient-specific surface for engaging a surface of a tibia; at least one tibia pin hole extending through the tibia pin guide; and a socket extending through the tibia pin guide; a talus pin guide that can comprise: a second patient-specific surface for engaging a surface of a talus; and at least one talus pin hole extending through the talus pin guide; and an interlocking component that can extend through the socket to position the tibia pin guide relative to the talus pin guide.

Example 2 can include, or can optionally be combined with the subject matter of Example 1, to optionally include a tibia pin guide that can comprise: an extension having the first patient-specific surface; a pin guide body having the at least one tibia pin hole; and a window body having the socket.

Example 3 can include, or can optionally be combined with the subject matter of one or any combination of Examples 1 or 2 to optionally include a first patient-specific surface that can be shaped to mate with an anterior surface of a distal portion of a tibia of a specific patient; a pin guide body that can extend from an edge of the extension away from the first patient-specific surface; and a window body that can extend from the pin guide body in a direction opposite that of the extension.

Example 4 can include, or can optionally be combined with the subject matter of one or any combination of Examples 1 through 3 to optionally include a talus pin guide that can comprise: a main body having the second patient-specific surface and through which the at least one talus pin hole extends; and at least one alignment feature that can extend from the main body from a surface opposite the second patient-specific surface, the at least one alignment feature can be configured to engage the interlocking component.

Example 5 can include, or can optionally be combined with the subject matter of one or any combination of Examples 1 through 4 to optionally include a second patient-specific surface that can be shaped to mate with an anterior surface of a proximal portion of a talus of a specific patient; and a center axis of the at least one alignment feature that can be parallel with a center axis of the at least one talus pin hole.

Example 6 can include, or can optionally be combined with the subject matter of one or any combination of Examples 1 through 5 to optionally include an interlocking component that can comprise: a pin body that can have at least one interlocking pin hole disposed to align with the at least one tibia pin hole; an extension that can extend from the pin body; and a lock that can extend from the extension in a direction of the pin body.

Example 7 can include, or can optionally be combined with the subject matter of one or any combination of Examples 1 through 6 to optionally include a shelf that can be formed by the window body and the pin guide body of the tibia pin guide, the pin body of the interlocking component can be configured to rest on the shelf when the extension is engaged with the window body and the lock extends into the socket; and the lock can include at least one alignment socket for receiving the at least one alignment feature.

Example 8 can include, or can optionally be combined with the subject matter of one or any combination of Examples 1 through 7 to optionally include a pair of tibia pins that can extend through a pair of tibia pin holes extending through the interlocking component and the tibia pin guide; and a pair of talus pins that can extend through a pair of talus pin holes in the tibia pin guide and a pair of recesses in the talus pin guide.

Example 9 can include or use subject matter such as a patient-specific cutting guide system for performing a total ankle arthroplasty, the patient-specific cutting guide system can comprise: a talus cutting guide that can comprise: a talus main body; a talus extension extending from the talus main body and having a first patient-specific surface configured to engage a surface of a tibia; and a cutting body extending from the talus main body in an opposite direction as the talus extension, the cutting body having a first cutting guide slot positioned to resect a talus; and a tibia cutting guide that can comprise: a tibia main body having a second cutting guide slot positioned to resect a tibia; a tibia extension having a second patient-specific surface configured to engage the surface of a tibia; and a flange forming a third cutting guide slot with the tibia main body.

Example 10 can include, or can optionally be combined with the subject matter of Example 9, to optionally include a talus main body that can include a window so that a joint line between the tibia and the talus can be viewed through the talus cutting guide when the first patient-specific surface is engaged with the tibia.

Example 11 can include, or can optionally be combined with the subject matter of one or any combination of Examples 9 or 10 to optionally include a talus main body that can include a pair of beams that form the window, the pair of beams offsetting the talus extension from the cutting body.

Example 12 can include, or can optionally be combined with the subject matter of one or any combination of Examples 9 through 11 to optionally include a cutting body that can have a third patient-specific surface configured to engage a surface of the talus.

Example 13 can include, or can optionally be combined with the subject matter of one or any combination of Examples 9 through 12 to optionally include a first cutting guide slot and a second cutting guide slot that can be positioned to be approximately parallel to a transverse plane of the tibia when the first and second patient-specific surfaces are engaged with the tibia, respectively; and a third cutting guide slot that can be disposed oblique to the second cutting guide slot.

Example 14 can include, or can optionally be combined with the subject matter of one or any combination of Examples 9 through 13 to optionally include a talus main body that can include a first pair of tibia pin holes and the cutting body includes a pair of talus pin holes; and a tibia main body that can include a second pair of tibia pin holes.

Example 15 can include or use subject matter such as a method of performing a total ankle arthroplasty, the method can comprise: coupling a patient-specific talus pin guide to a talus; coupling a patient-specific tibia pin guide to a tibia; positioning an interlocking device between the patient-specific tibia pin guide and the patient-specific talus pin guide; inserting guide pins into the patient-specific tibia and talus pin guides; removing the patient-specific talus and tibia pin guides from the guide pins; and coupling patient-specific talus and tibia cutting guides to the talus and tibia using at least some of the guide pins to alternatively perform resections on the tibia and talus.

Example 16 can include, or can optionally be combined with the subject matter of Example 15, to optionally include patient-specific talus and tibia cutting guides that can be positioned to guide resections on the talus and tibia from an anterior approach.

Example 17 can include, or can optionally be combined with the subject matter of one or any combination of Examples 15 or 16 to optionally include moving an ankle joint through flexion to move the talus relative to the tibia to align the patient-specific talus pin guide with a window in the patient-specific tibia pin guide.

Example 18 can include, or can optionally be combined with the subject matter of one or any combination of Examples 15 through 17 to optionally include inserting the interlocking device into the window to engage the patient-specific talus pin guide and to align the patient-specific talus pin guide with the patient-specific tibia pin guide.

Example 19 can include, or can optionally be combined with the subject matter of one or any combination of Examples 15 through 18 to optionally include viewing a joint line between the tibia and talus through a window in the patient-specific talus cutting guide when resecting the talus.

Example 20 can include, or can optionally be combined with the subject matter of one or any combination of Examples 15 through 19 to optionally include performing a first resection of the tibia using the patient-specific tibia cutting guide along a distal surface of the tibia and performing a second resection of the tibia using the patient-specific tibia cutting guide along a lateral surface of a medial malleolus of the tibia.

Each of these non-limiting examples can stand on its own, or can be combined in various permutations or combinations with one or more of the other examples.

The above detailed description includes references to the accompanying drawings, which form a part of the detailed description. The drawings show, by way of illustration, specific embodiments in which the invention can be practiced. These embodiments are also referred to herein as "examples." Such examples can include elements in addition to those shown or described. However, the present inventors also contemplate examples in which only those elements shown or described are provided. Moreover, the present inventors also contemplate examples using any combination or permutation of those elements shown or described (or one or more aspects thereof), either with respect to a particular example (or one or more aspects thereof), or with respect to other examples (or one or more aspects thereof) shown or described herein.

In the event of inconsistent usages between this document and any documents so incorporated by reference, the usage in this document controls.

In this document, the terms "a" or "an" are used, as is common in patent documents, to include one or more than one, independent of any other instances or usages of "at least one" or "one or more." In this document, the term "or" is used to refer to a nonexclusive or, such that "A or B" includes "A but not B," "B but not A," and "A and B," unless otherwise indicated. In this document, the terms "including" and "in which" are used as the plain-English equivalents of the respective terms "comprising" and "wherein." Also, in the following claims, the terms "including" and "comprising" are open-ended, that is, a system, device, article, composition, formulation, or process that includes elements in addition to those listed after such a term in a claim are still deemed to fall within the scope of that claim. Moreover, in the following claims, the terms "first," "second," and "third," etc. are used merely as labels, and are not intended to impose numerical requirements on their objects.

Method examples described herein can be machine or computer-implemented at least in part. Some examples can include a computer-readable medium or machine-readable medium encoded with instructions operable to configure an electronic device to perform methods as described in the above examples. An implementation of such methods can include code, such as microcode, assembly language code, a higher-level language code, or the like. Such code can include computer readable instructions for performing various methods. The code may form portions of computer program products. Further, in an example, the code can be tangibly stored on one or more volatile, non-transitory, or non-volatile tangible computer-readable media, such as during execution or at other times. Examples of these tangible computer-readable media can include, but are not limited to, hard disks, removable magnetic disks, removable optical disks (e.g., compact disks and digital video disks), magnetic cassettes, memory cards or sticks, random access memories (RAMs), read only memories (ROMs), and the like.

The above description is intended to be illustrative, and not restrictive. For example, the above-described examples (or one or more aspects thereof) may be used in combination with each other. Other embodiments can be used, such as by one of ordinary skill in the art upon reviewing the above description. The Abstract is provided to comply with 37 C.F.R. § 1.72(b), to allow the reader to quickly ascertain the nature of the technical disclosure. It is submitted with the understanding that it will not be used to interpret or limit the scope or meaning of the claims. Also, in the above Detailed Description, various features may be grouped together to streamline the disclosure. This should not be interpreted as intending that an unclaimed disclosed feature is essential to any claim. Rather, inventive subject matter may lie in less than all features of a particular disclosed embodiment. Thus, the following claims are hereby incorporated into the Detailed Description as examples or embodiments, with each claim standing on its own as a separate embodiment, and it is contemplated that such embodiments can be combined with each other in various combinations or permutations. The scope of the invention should be determined with reference to the appended claims, along with the full scope of equivalents to which such claims are entitled.

Following from the above description and invention summaries, it should be apparent to those of ordinary skill in the art that, while the methods and apparatuses herein described constitute exemplary embodiments of the present invention, it is to be understood that the inventions contained herein are not limited to the above precise embodiment and that changes may be made without departing from the scope of the invention as defined by the following proposed points of novelty. Likewise, it is to be understood that it is not necessary to meet any or all of the identified advantages or objects of the invention disclosed herein in order to fall within the scope of the invention, since inherent and/or unforeseen advantages of the present invention may exist even though they may not have been explicitly discussed herein.

The claimed invention is:

1. A patient-specific pin guide for performing a total ankle arthroplasty, the patient-specific pin guide comprising:
    a tibia pin guide comprising:
        a first patient-specific surface for engaging a surface of a tibia; and
        a first tibia pin hole extending through the tibia pin guide;
    a foot pin guide comprising:
        a second patient-specific surface for engaging a surface of a foot bone;
        a first foot pin hole extending through the foot pin guide; and a first foot guide hole extending through the foot pin guide; and an interlocking component configured to couple the tibia pin guide and the foot pin guide to each other such that the first patient-specific surface and the second patient-specific surface are oriented in a patient-specific orientation on opposite sides of an interface between the tibia and the foot bone;

wherein the interlocking component is configured to couple the tibia pin guide and the foot pin guide to each other without the tibia pin guide and the foot pin guide contacting each other.

2. The patient-specific pin guide of claim 1, further comprising:
a second tibia pin hole extending through the tibia pin guide;
a second foot pin hole extending through the foot pin guide;
a second foot guide hole extending through the foot pin guide; and
first and second tibia guide holes extending through the tibia pin guide;
wherein the first and second tibia pin holes, the first and second foot pin holes, the first and second tibia guide holes and the first and second foot guide holes are all parallel to each other.

3. The patient-specific pin guide of claim 1, wherein:
the tibia pin guide further comprises:
a first planar superior-inferior surface; and
a first planar medial-lateral surface; and
the interlocking component further comprises:
a second planar superior-inferior surface; and
a second planar medial-lateral surface;
wherein the first planar superior-inferior surface is configured to flushly engage the second planar superior-inferior surface, and the first planar medial-lateral surface is configured to flushly engage the second planar medial-lateral surface to squarely lock the tibia pin guide and the interlocking component.

4. The patient-specific pin guide of claim 3, wherein:
the first patient-specific surface comprises an irregularly shaped surface having contours that closely match with or form a mirror image of the tibia of a specific patient; and
the second patient-specific surface comprises an irregularly shaped surface having contours that closely match with or form a mirror image of the foot bone of the specific patient.

5. The patient-specific pin guide of claim 1, further comprising:
a socket located in the tibia pin guide to receive the interlocking component; and
first locking features located on the foot pin guide, the locking features configured to engage the interlocking component when the interlocking component is positioned in the socket.

6. The patient-specific pin guide of claim 5, wherein the interlocking component further comprises second locking features to engage the first locking features.

7. The patient-specific pin guide of claim 6, wherein the first and second locking features comprise pyramid shaped projections and sockets extending in an anterior-posterior direction.

8. The patient-specific pin guide of claim 1, wherein:
the first tibia pin hole and the first foot guide hole axially align when the interlocking component couples the tibia pin guide and the foot pin guide; and the first foot pin hole, the first foot guide hole and the first tibia pin hole extend generally perpendicularly to a mechanical axis of the tibia.

9. A patient-specific pin guide for performing a total ankle arthroplasty on a specific patient, the patient-specific pin guide comprising:
a tibia pin guide comprising:
a first patient-specific surface for engaging an anterior surface of a tibia;
at least one tibia pin hole extending through the tibia pin guide along a first axis in an orientation to direct a pin into the anterior surface of the tibia; and
a socket extending through the tibia pin guide along a second axis, the socket located spaced apart from and to not penetrate the first patient-specific surface;
a talus pin guide comprising:
a second patient-specific surface for engaging an anterior surface of a talus; and
at least one talus pin hole extending through the talus pin guide along a third axis in an orientation to direct a pin into the anterior surface of the talus; and
an interlocking component that can extend through the socket to position the tibia pin guide relative to the talus pin guide such that the first patient-specific surface of the tibia pin guide and the second patient-specific surface of the talus pin guide are spaced apart across an interface between the tibia and the talus in a superior-inferior direction and in orientations such that the first patient-specific surface and the second patient-specific surface can simultaneously engage the anterior surface of the tibia and the anterior surface of the talus respectively,
wherein the interlocking component is configured to position the talus pin guide posteriorly of an adjacent portion of the tibia pin guide.

10. The patient-specific pin guide of claim 9, wherein the tibia pin guide comprises:
an extension having the first patient-specific surface, the extension having a major axis extending in the superior-inferior direction;
a pin guide body having the at least one tibia pin hole, the pin guide body having a major axis extending in an anterior-posterior direction; and
a window body having the socket, the socket extending in the anterior-posterior direction along the second axis.

11. The patient-specific pin guide of claim 10, wherein:
the first patient-specific surface comprises an irregularly shaped surface having contours that closely match with or form a mirror image of the tibia such that the first patient-specific surface is shaped to mate with the anterior surface of a distal portion of the tibia of the specific patient;
the pin guide body extends from an edge of the extension away from the first patient-specific surface;
the extension extends from the pin guide body in a superior direction from a posterior portion of the pin guide body; and
the window body extends from the pin guide body in an inferior direction from an anterior portion of the pin guide body.

12. The patient-specific pin guide of claim 11, wherein the talus pin guide comprises:
a main body having the second patient-specific surface and through which the at least one talus pin hole extends; and
at least one alignment feature extending from the main body from a surface opposite the second patient-specific surface, the at least one alignment feature configured to engage the interlocking component.

13. The patient-specific pin guide of claim 12, wherein:
the second patient-specific surface comprises an irregularly shaped surface having contours that closely match with or form a mirror image of the talus such that the second patient-specific surface is shaped to mate with the anterior surface of a proximal portion of the talus of the specific patient; and
a center axis of the at least one alignment feature is parallel with the third axis.

14. The patient-specific pin guide of claim 12, wherein the interlocking component comprises:
a pin body having at least one interlocking pin hole disposed to align with the at least one tibia pin hole;
an extension extending from the pin body; and
a lock extending from the extension in a direction of t pin body.

15. The patient-specific pin guide of claim 14, wherein:
the window body and the pin guide body of the tibia pin guide form a shelf, and the pin body of the interlocking component is configured to rest on the shelf when the extension is engaged with the window body and the lock extends into the socket; and
the lock includes at least one alignment socket for receiving the at least one alignment feature.

16. The patient-specific pin guide of claim 9, further comprising:
a pair of tibia pins extending through a pair of tibia pin holes extending through the interlocking component and the tibia pin guide, the pair of tibia pin holes including the at least one tibia pin hole; and
a pair of talus pins extending through a pair of talus pin holes in the tibia pin guide and a pair of recesses in the talus pin guide.

17. The patient-specific pin guide of claim 9, wherein:
the first axis and the third axis are parallel to the second axis; and
the first axis and the third axis are not co-axial.

18. A method of performing a total ankle arthroplasty, the method comprising:
coupling a patient-specific talus pin guide to a talus, the patient-specific talus pin guide comprising:
a first patient-specific surface for engaging a surface of the talus;
a first talus pin hole extending through the talus pin guide; and
a first talus guide hole extending through the talus pin guide;
coupling a patient-specific tibia pin guide to a tibia, the patient-specific tibia pin guide comprising:

a second patient-specific surface for engaging a surface of the tibia; and
a first tibia pin hole extending through the tibia pin guide;
positioning an interlocking device between the patient-specific tibia pin guide and the patient-specific talus pin guide such that the first patient-specific surface is oriented relative to the second patient-specific surface in a patient-specific orientation on opposite sides of an interface between the talus and the tibia, wherein the interlocking device is configured to couple the tibia pin guide and the talus pin guide to each other without the tibia pin guide and the talus pin guide contacting each other;
inserting guide pins into the patient-specific tibia and talus pin guides;
removing the patient-specific talus and tibia pin guides from the guide pins; and
coupling patient-specific talus and tibia cutting guides to the talus and the tibia using at least some of the guide pins to alternatively perform resections on the talus and the tibia;
wherein the first tibia pin hole and the first talus guide hole axially align when the interlocking device couples the tibia pin guide and the talus pin guide; and
wherein the first talus pin hole, the first talus guide hole and the first tibia pin hole extend generally perpendicularly to a mechanical axis of the tibia.

19. The method of claim 18, wherein the patient-specific talus and tibia cutting guides are positioned to guide resections on the talus and the tibia from an anterior approach, the method further comprising performing a first resection of the tibia using the patient-specific tibia cutting guide along a distal surface of the tibia and performing a second resection of the tibia using the patient-specific tibia cutting guide along a lateral surface of a medial malleolus of the tibia.

20. The method of claim 18, further comprising:
moving an ankle joint through flexion to move the talus relative to the tibia to align the patient-specific talus pin guide with a window in the patient-specific tibia pin guide;
viewing a joint line between the tibia and the talus through a window in the patient-specific talus cutting guide when resecting the talus; and
inserting the interlocking device into the window in the patient-specific tibia pin guide to engage the patient-specific talus pin guide and to align the patient-specific talus pin guide with the patient-specific tibia pin guide.

* * * * *

UNITED STATES PATENT AND TRADEMARK OFFICE
CERTIFICATE OF CORRECTION

Page 1 of 1

PATENT NO. : 10,881,417 B2
APPLICATION NO. : 15/177871
DATED : January 5, 2021
INVENTOR(S) : Mohamed Mahfouz It is certified that error appears in the above-identified patent and that said Letters Patent is hereby corrected as shown below:

In the Claims

In Column 20, Line 31, in Claim 9, delete "talus" and insert --talus,-- therefor In Column 21, Line 17, in Claim 14, delete "t" and insert --the-- therefor Signed and Sealed this
Sixteenth Day of March, 2021

Drew Hirshfeld
*Performing the Functions and Duties of the*
*Under Secretary of Commerce for Intellectual Property and*
*Director of the United States Patent and Trademark Office*